(12) United States Patent
Konishi

(10) Patent No.: US 8,340,781 B2
(45) Date of Patent: Dec. 25, 2012

(54) SENSOR ELEMENT, SENSOR SYSTEM, CATHETER AND MANUFACTURING METHOD OF THE SENSOR ELEMENT

(75) Inventor: Satoshi Konishi, Tokyo (JP)

(73) Assignee: Namiki Seimitsu Houseki Kabushiki Kaisha (JP)

( * ) Notice: Subject to any disclaimer, the term of this patent is extended or adjusted under 35 U.S.C. 154(b) by 142 days.

(21) Appl. No.: 12/468,658

(22) Filed: May 19, 2009

(65) Prior Publication Data
US 2009/0292242 A1 Nov. 26, 2009

(30) Foreign Application Priority Data
May 22, 2008 (JP) ................................. 2008-134600

(51) Int. Cl.
*A61N 1/00* (2006.01)
(52) U.S. Cl. .................... 607/116; 600/547; 29/592.1
(58) Field of Classification Search .................. 600/547; 607/65, 116; 29/592.1
See application file for complete search history.

(56) References Cited

U.S. PATENT DOCUMENTS

| | | | |
|---|---|---|---|
| 2,582,314 A | | 1/1952 | Doll |
| 2,582,315 A | | 1/1952 | Doll |
| 5,323,659 A | * | 6/1994 | Wakamiya et al. ......... 73/862.28 |
| 5,545,206 A | * | 8/1996 | Carson ........................... 607/126 |
| 5,684,341 A | * | 11/1997 | Steingroever .................... 307/16 |
| 5,991,650 A | * | 11/1999 | Swanson et al. ............... 600/374 |
| 2002/0013537 A1 | * | 1/2002 | Rock .............................. 600/547 |
| 2002/0153886 A1 | * | 10/2002 | Kawakami ..................... 324/253 |
| 2004/0230131 A1 | * | 11/2004 | Kassab et al. ................. 600/547 |
| 2006/0253181 A1 | * | 11/2006 | Schulman et al. ............. 607/116 |
| 2008/0294041 A1 | * | 11/2008 | Kassab .......................... 600/433 |
| 2009/0234378 A1 | * | 9/2009 | Escudero et al. ............. 606/180 |

FOREIGN PATENT DOCUMENTS

| | | |
|---|---|---|
| JP | 06-342081 | 12/1994 |
| JP | 2009-502321 | 1/2009 |

OTHER PUBLICATIONS

Y. Inaba; "Electronics circuit in experimental study"; Electronics Life; Japan Broadcast Publishing Association; Jun. 1993; No. 730; pp. 146-152.
Shinsuke Nanto et al.; "Illustration/Cardiac Catheter Therapy/From Diagnostic to Intervention"; Sep. 25, 2005.
J.H. Moran et al.; "Basic Theory of Induction Logging and Application to Study of Two-Coil Sondes"; Geophysics; vol. XXVII, No. 6, Part 1, Dec. 1962, pp. 829-858.
W.C. Duesterhoeft, Jr. et al.; "The Effect of Coil Design on the Performance of the Induction Log"; Society of Petroleum Engineers Office, Aug. 2, 1960, Revised manuscript, Paper presented at 35th Annual Fall Meeting of SPE, Oct. 2-5, 1960, Denver, CO.

\* cited by examiner

*Primary Examiner* — Nicholas D Luccheshi
*Assistant Examiner* — Gerald Landry, II
(74) *Attorney, Agent, or Firm* — Studebaker & Brackett PC; Donald R. Studebaker

(57) ABSTRACT

A sensor element, a sensor system, a catheter that can detect the thrombi, plaques and stents in the blood vessels and manufacturing method of the sensor element are provided. A cylinder is formed as a cylinder shaped part that has a long inner space and one open end. The cylinder has a slit being formed along an axis and the width of the slit is less than diameter of the inner space. A plurality of coils is wound outside of the cylinder and the lead portions of the coils are led into the inner space of the cylinder by passing through the slits. Electrically conducting means are connected to each of lead portions and are externally led out from the open end of the cylinder.

20 Claims, 21 Drawing Sheets

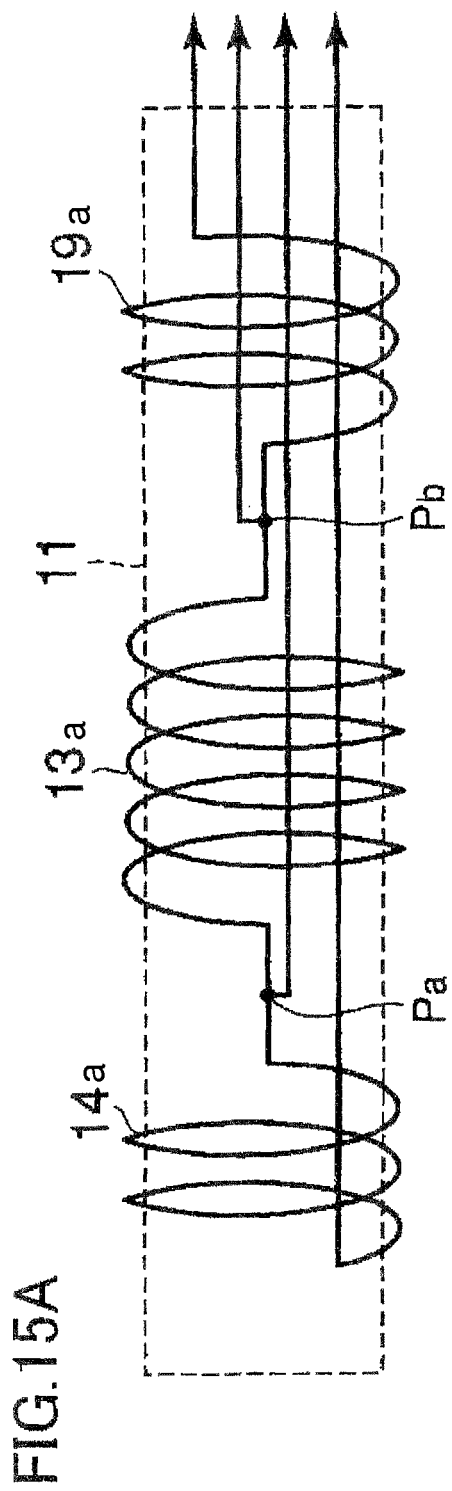

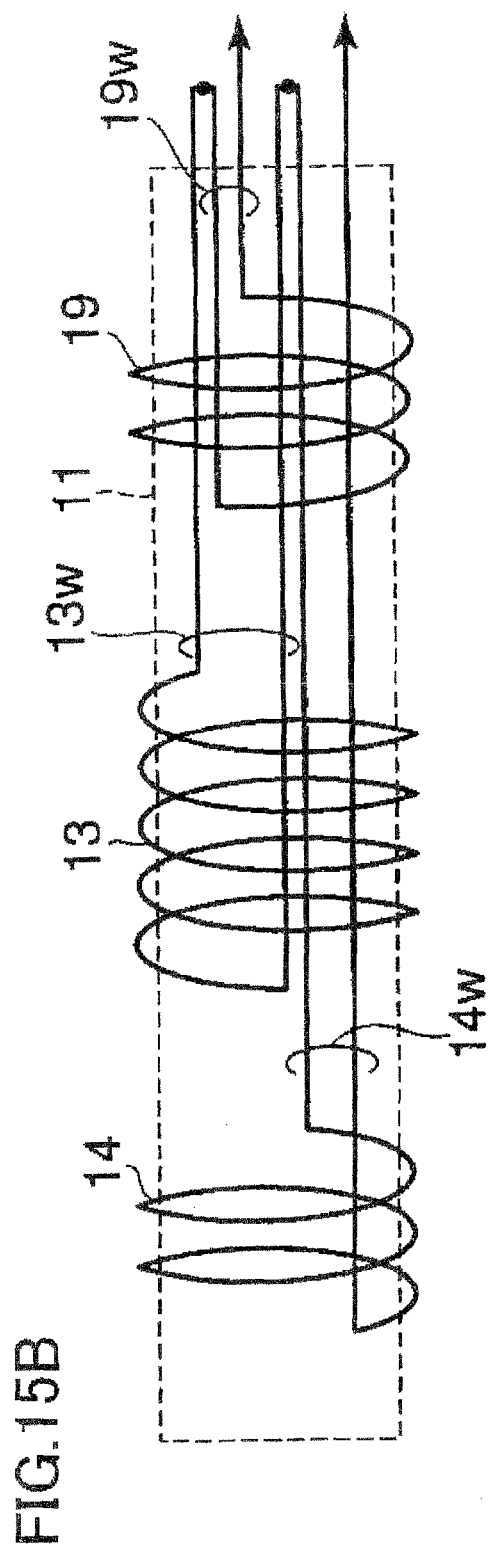

SENSOR ELEMENT, SENSOR SYSTEM, CATHETER AND MANUFACTURING METHOD OF THE SENSOR ELEMENT

FIELD OF THE INVENTION

The present invention generally pertains to medical equipment, and, more particularly, to sensor elements and sensor element system utilized to sense physical, physiological and morphological parameters of plaques, thrombosis, tissues and stents installed in a blood vessel, and to catheters that comprise the sensor elements and to manufacturing methods of the sensor elements.

BACKGROUND OF THE INVENTION

Sclerosis of the arteries, myocardial infarction (or angio stenosis) and cerebral thrombosis and ischemic cerebral infarction are caused by choking or decreasing of blood flow due to stenosis formed in an artery, cerebral vessel and coronary arteries. Thrombosis is generated by clot on the blood vessel or inflammation of blood vessel and expansion or hardening of atheromatous plaques between the media and endothelium of arteries or blood vessels. Angiography is a well-known diagnosis to find clots, thromboses or plaques. A fine blood catheter is inserted into a blood vessel and injects contrast medium therethrough. The blood flow is observed by the flow of the contrast medium that is observable by X-ray, which is blocked by contrast medium and less-blocked by the human body of a patient. Catheters are usually percutaneously inserted through the femoral veins and are pushed up to the target portion of the veins or arteries. Then, the contrast medium is injected into the blood flow through the catheter. Since the contrast medium has less transparency against the X-ray, we can have a image such that the vein or arteries, of which a downstream vessel is narrowed or choked by clots or atheromasclerosis, is visualized by the shadow of X-ray such that the narrowed or choked vessel and the upper stream vessels are shown as shadowed areas, and the other body portions as unshadowed areas. By this evaluation method, it is possible to find vessels which have the narrowed or choked portions in their down streams and narrowed or choked vessel (i.e., Sclerosis) portion.

Once infarction is found and diagnosed as thrombus or sclerosis, thrombus dissolvers or stents installed in the blood vessels are used as treatment. Statin (a trade mark: HMG-CoA reductase enzyme inhibitor) is widely used for thrombus dissolver. Stents are cylindrical metal meshes and made from metal tubes. Stents can be expanded in the blood vessels by balloon catheters. Stents are used for the operation of thrombus and coronary disease. A stent is inserted in a balloon catheter in minimum-diameter state (i.e., shrunken state), or a stent made from a metal tube is inserted in the blood vessel with surfaces of the balloon catheter in a shrunken state and pushed into the blood vessel so that the diameter of the balloon catheter is of a minimum dimension. The catheter to which the stent is attached travels inside the blood vessels, and the balloon is inflated when the catheter reaches the infarction portion of the blood vessel. The diameter of the stent is increased by the expansion or inflation of the balloon. Therefore, the infarction portion of the blood vessel is pushed outwards by increasing the diameter of the stent so that infarction is cleared. The diameter of the stent is maintained by the inflated balloon. After the stent is inflated in the blood vessel, the balloon is shrunken to the original size and the image of the blood vessel is taken by using contrast medium and X-ray. By comparing two images of the blood vessel, such as that before and after the stent is inserted, it is confirmed whether or not the insertion of the sent has been properly carried out. If the image of the contrast medium flow in the position where the stent stays in the blood vessel has the same shape of the flow in other positions along the blood vessel, then it can be deduced that the stent is properly inserted and widened in the infarction portion of the blood vessel such that the infarction is successfully removed.

SUMMARY OF THE INVENTION

For contrast media, a non-ionic iodine water solvent contrast medium, an iodine water solvent contrast medium or low permeable iodine water solvent contrast medium is used. However, these contrast media may be health-adverse and have physiological side effect. The causes of adverseness or side-effect are classified into (1) physical characteristics of the contrast media, (2) chemical toxics of the contrast media, (3) anaphylactic reaction, and (4) psychological factors. The causes (1) and (2) are the volumetric reactions related to high-permeability, non-hydrophilic ionization load of the contract media. The cause (3) is based on non-volumetric dependent allergic reaction, such as free reagent of chemical transporting materials, immunological reactions as positive antigen-antibody reaction. The cause (3) is heavily adverse to the function of kidneys. Each symptom seen as the actual side effects during the operation is caused by various complex factors. For example, a sneeze, rash, fever, pain of vessels, vomit, cold sweat, pale face, lower blood pressure or dyspnea may represent a symptom of a side effect. According to these side effects, the quantity and time for using of contrast media is limited. As the results, it is sometime difficult to carry out a series of operation from detecting the infarction of the blood vessel and to fully confirming the completion of stent insertion to the infarction of the blood vessel. This difficulty may create the necessity to re-insert new stents afterwards.

For the detection of the infarction of blood vessels and the confirmation of the insertion of stents, X-ray projection is necessarily used for the diagnostic. However, during the procedure, both patients and surgeons are definitely and directly exposed to X-ray.

By using the X-ray image of blood vessel, it is difficult to specify the precise position of the infarction of the blood vessel due to the blood vessel constantly moving with each heart pulse, faint contrast of the image caused by low organic density contrast and contrast media disappearance in the blood flow. For these reasons, appropriate insertion of stents to the specific portion of the blood vessels is very difficult and re-insertion of new stents may be necessary afterwards. However, because of the difficulty of removing inserted stents from the blood vessels, the number of times for such an operation is limited.

It is also difficult to detect vulnerable plaque, which grows between adventitia and media arteries and extends to outwardly from the blood vessel. The vulnerable plaques do cause infarctions in the blood vessels. It is difficult to find the vulnerable plaques from the X-ray image when no infarction is formed inside of the blood vessels. However the vulnerable plaques turn into crystallization and break the adventitia of arteries and cause arterial rupture that results in mortal bleeding. Unfortunately, there is no life preserving treatment for such a bleeding.

According to the problems discussed above, the present invention provides a sensor technology and its application by which thrombi, plaques and stents may be detected. Further objects and advantages of the present invention will become apparent to those skilled in the art upon reading and understand the following derailed description and the accompanying drawings.

Patented Reference 1: U.S. Pat. No. 2,582,315 issued Jan. 15, 1952 to Henri-Georges Doll discloses an induction logging sensor that exploits a technology of measuring the physical properties of the substance surrounding the sensor.

Patented Reference 2: U.S. Pat. No. 2,582,314 issued Jan. 15, 1952 to Henri-Georges Doll discloses an induction logging sensor that exploits a technology of determining the physical properties of the substance surrounding the sensor.

Non-Patented Reference 1: Basic Theory of Induction Logging and Application to Study of Two-coil Sondes, J. H. Moran and K. S. Kunz, Geophysics, Vol. XXVII, No. 6, Part I, pp. 829-858, 1962 discloses a two-coil system of the induction sensor discloses an induction logging sensor that exploits a technology of measuring and determining the physical properties of the substance surrounding the sensor.

Non-Patented Reference 2: The Effect of Coil Design on the Performance of the Induction Log, W. C. Duesterhoeft, Jr., et. al., Journal of Petroleum Technology, PP. 1137-1150, November, 1961 discloses a response to the electrical conductive material that is the formation conductivity induction logging sensor that exploits another technology of measuring and determining the physical properties of the substance surrounding the sensor.

Non-Patented Reference 3: "Illustration/Cardiac Catheter Therapy/From Diagnostic to Intervention", Shinsuke Nanto, et. al., 25 th Sep. 2005 discloses the configuration and therapeutic usage of cardiac catheters.

BRIEF DESCRIPTION OF THE DRAWINGS

FIG. 15A is a drawing of a cable connection of the signal receiving coil 13 and the spatially differentiating coils 14 and 19.

FIG. 15B shows a drawing that shows an example of modification of the cable connection of the signal receiving coil 13 and the spatially differentiating coils 14 and 19.

FIG. 16 is a drawing of an example of the modification with regard to forming of the slit 11a.

DESCRIPTION OF THE PRESENT INVENTION

Figure 1:
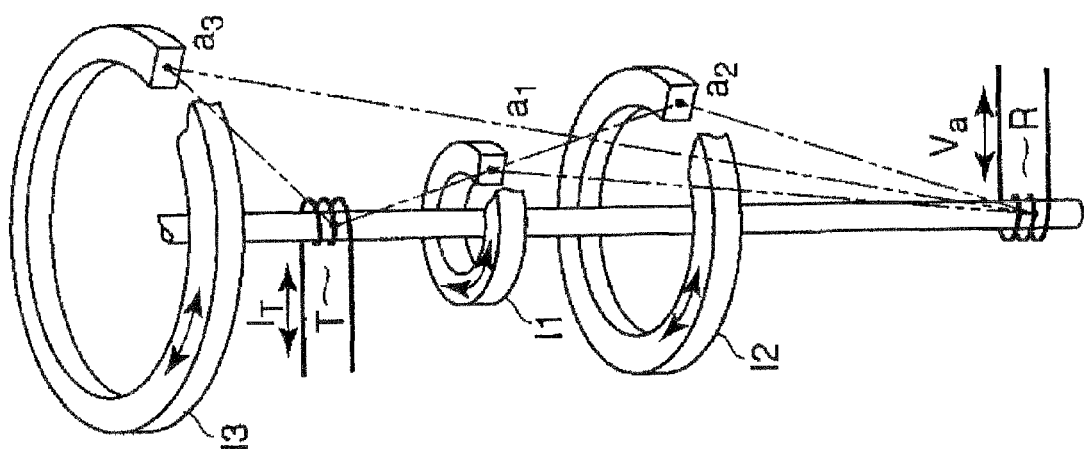
FIG. 1 shows the principle of the ILS (Induction Logging Sensor) on which embodiments of the present invention are based.

A first embodiment of the present invention is a sensor element that comprises a cylinder (i.e., a cylindrical shaped part) having an open end at least one end thereof and a slit being formed along an axis thereof, wherein the width of the slit is less than diameter of an inner space thereof. The sensor further includes a coil element group that has more than two sets of a coil element, which is an electrical coil that includes a wound wire portion that comprises more than one wound wire having one winding direction, and two lead portions formed at both ends of the wound wire portion, wherein the wound wire portion is formed on a surface of the cylinder, and the two lead portions are led into the inner space of the cylinder by passing through the slit, and more than two sets of a pair of electrically conducting means set in the inner space and electrically connected to each of the two lead portions and is externally led out from the open end of the cylinder.

A second embodiment of the present invention is a sensor element that has the same coil sensor element as the first embodiment of the present invention, wherein the coil element group comprises a first coil element and a second coil element, of which the second coil element includes a first wound wire portion with one winding direction and a second wound wire portion having a fewer number of wound turn than the first wound wire portion, and a third wound wire portion both with the other winding direction than the one winding direction in a configuration, the first wound wire portion locates between the second wound wire portion and the third wound wire portion, the second wound wire portion locates between the first wound wire portion and the first coil element, one end of the first wound wire portion and one end of the second wire portion are electrically connected through a first electrically connecting portion, the two sets of lead portions are formed at the other end of the second wound wire portion and the other end of the third wound wire portion.

A third embodiment of the present invention is a sensor system that comprises a coil element group which is a first kind of sensor element that comprises a first coil element and a second coil element, wherein the first coil element has a wound wire portion including a wound wire with one winding direction, and the second coil element has a wound wire portion including a first wound wire with one winding direction and a second wound wire with the other winding direction than the one winding direction in a configuration wherein the first wound wire and the second wound wire are electrically connected through an electrically connecting portion, and is a first kind of coil element. The sensor may include a second kind of sensor element that comprises a first coil element and a second coil element, wherein a first coil element is same as the above first coil element, and the second coil element includes a first wound wire portion with one winding direction and a second wound wire portion having a fewer number of wound turn than the first wound wire portion, and a third wound wire portion both with the other winding direction than the one winding direction in a configuration the first wound wire portion locates between the second wound wire portion and the third wound wire portion, the second wound wire portion locates between the first wound wire portion and the first coil element, and one end of the first wound wire portion and one end of the second wire portion are electrically connected through a first electrically connecting portion the other one end of the first wound wire portion, and one end of the third wire portion electrically connected through a second electrically connecting portion. The third embodiment may alternatively include a third kind of sensor element that comprises a first coil element and a second coil element, wherein the second coil element is same as one of the above first coil elements, and a first coil element has a wound wire portion including a wound wire with one winding direction, and a second wound wire with the other winding direction than the one winding direction in a configuration wherein the first wound wire and the second wound wire are electrically connected through an electrically connecting portion. The embodiment further comprises an exciting signal generator and a signal receiving circuit, wherein the first coil element is excited by an exciting signal generated by the exciting signal generator via a the pair of electrically conducting means, and the second coil element is connected to a signal receiver circuit that receives an induced signal therein via another the pair of electrically conducting means.

A fourth embodiment of the present invention is a catheter that comprises a catheter sheath in form of a tube, a sensor element of the first embodiment, a cable electrically connected to an electrically conducting means included in said sensor element and set in an inner space of the catheter sheath.

A fifth embodiment of the present invention is a manufacturing method that comprises a step wherein a plurality of coil elements that are electrical coils each including at least one wound wire portion, two lead portions formed in both ends of such at least one wound wire portion is formed by using a plurality of electrical wires, a step wherein an electrical wire that is set external of the wound wire in a direction of center axis of the wound wire is connected to one of the two lead portions that is a extension of one of the two lead portions and another electrical wire that is set inside of the wound wire is connected to the other of the two lead portions or is a extension of the other of the two lead portions and set external of the wound wire, and a step wherein each of the plurality of coil elements is inserted into a cylinder (i.e., a cylindrical shaped part) having an open end at least one end thereof, and a slit being formed along the axis thereof, wherein the width of the slit is less than the diameter of an inner space thereof so that the coil elements surrounds the cylinder and both lead portions of the coil element are inserted into the inner space from the open end of the cylinder by sliding along the slit in a form wherein the lead portions extend into the inner space of the cylinder through the slit and a terminal of the electrical wires which are connected to the coil element so that a terminal of extension of each of the two lead portions extends to external of the inner space of the cylinder through the open end of the cylinder.

According to the present invention, it is possible to detect the existing of thrombi, plaques and stents in blood vessels.

The details of the present invention will be discussed hereinafter with drawings representing aspects of the each of the embodiments of the present invention. However, the present invention is not only limited to the specific embodiments discussed above but also those understood by the persons who have the knowledge of the field of the technologies related to the present invention with the information of the following description and technically common understanding and comprehension at the present time.

Before discussing the details of the embodiment of the present invention, fundamental technologies from which the present inventions are created are explained as follows.

Such fundamental technologies are typically specified as referred to the patent references 1 and 2 and non-patent references 1 and 2. These technologies are regarding induction logging sensor (hereinafter ILS).

The FIG. 1 shows the principle of the ILS.

By using a signal receiving coil element R, the ILS can acquire the induced phenomena (presented by induced currents I1, I2 and I3) that reveal when the signal exciting coil element T is excited by an alternative signal to measure the electrical characteristics of the surroundings around the signal exciting coil element and it is possible to identify the substance that stays around the signal exciting coil element T and measures the distance of such subject apart from the ILS.

Figure 2:
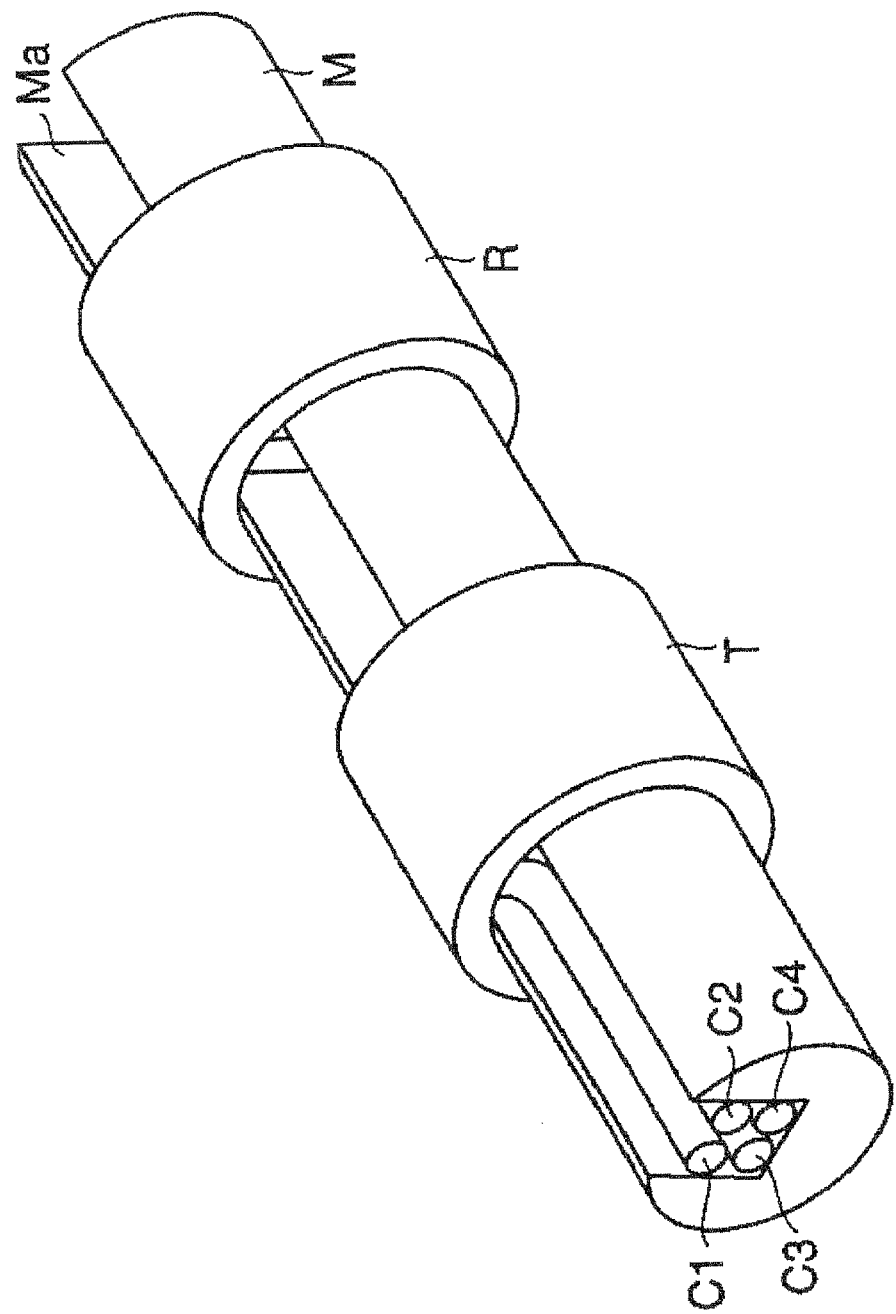
FIG. 2 is an oblique perspective drawing of an example of the ILS.

FIG. 2 shows an example of the oblique perspective drawing of the ILS.

This ILS includes a mandrel M, signal exciting coil element T, signal receiving coil element R and cables C1, C2, C3 and C4.

The mandrel M is a central part of the structure of this ILS and is formed into column shape with non-magnetic material. The signal exciting coil element T and the signal receiving coil R are wound around the outer surface of the mandrel M. The cables C1 and C2 connect with the signal exciting coil element T and an exciting signal generator. The cables C3 and C4 connect with the signal receiving coil element R and the signal receiving circuit that is not shown in FIG. 2. The mandrel M has a groove where the cables C1 to C4 are accommodated. The ILS is covered with an insulating pipe, which is not shown in FIG. 2, around the overall structure shown in FIG. 2, and is protected from the outside environment by the insulating pipe.

Blood flow, thrombi, plaques and stents have different electrical conductivities, therefore it is possible to adopt the principle used in the above-described ILS in order to detect their existence and measure the diameters or physical dimensions thereof.

However, existing ILS cannot be used for the detection of thrombi, plaques or stents due to the reasons explained bellows.

(Structural Difficulty)

Since the primary purpose of the above-described ILS is to explore oil in the field, it is used in a way such that it is drop into an open hole drilled in the ground by using a physically large drill. Therefore, the diameter of ILS is 3⅜ or 1½ inches. The open hole is drilled in a straight form as the ILS since ILS is required not to be bent. However, the sensor element that is for the measurement of the thrombi, plaques and stents must be insertable into blood vessels. Hence, for this medical purpose, the sensor element has to be shrunken down to a compact size. For example, in order to insert the sensor element into the coronary arteries, the outer diameter of the sensor element has to be roughly less than 1.5 mm. Since the blood vessels have straight portions and curved portions, it is preferred that the sensor can conform the outer shape in accordance to the inner shapes of the blood vessels.

However, using the design of the known ILS, we cannot obtain enough cross sectional areas that can accommodate the cables in the sensor element when the ILS physical shape is merely shrunken and as the structure is maintained as is. In addition, the mandrel M as shown in FIG. 2 still maintains groove structure which is rather large compared to the cross section area such that the mandrel M is not easily bent in accordance with the structure in which the mandrel M is to be inserted.

Once the cross section of the groove Ma has been increased for the purpose of increasing accommodation of cables and flexibility to be bent, such an increase of the shape causes extremely decreasing of mechanical durability of the mandrel M, since the thickness between outer surface of the mandrel M and the medial crest, which is the line between the wall surface and bottom one of the groove Ma, has been significantly reduced.

(Measurement Difficulty)

Further, the conventional ILS is to judge the liquid in the formation to which an open hole, which is filled with oil-base mud and the ILS is inserted thereto, is drilled, whether it is brine or oil. The actual measurement by using ILS is to differentiate the electrical conductive brine from non-conductive oil-base mud and non-conductive oil from non-conductive oil-base mud.

However, for the actual measurement by using a sensor element which is shrunken down from the conventional ILS, wherein the sensor is inserted into a blood vessel and detects thrombi or plaques, it is necessary to measure electrically low conductive thrombi or plaques via blood, which is rather electrically conductive. Therefore, the difference of the electrical conductivities of those two substances that need to be differentiated is small, and it is difficult to analyze the electrical characteristics inherent to thrombi and plaques.

We will now explain a preferred embodiment of a sensor element that is suitable to detect thrombi, plaques and stents by using the principle of the above ILS and a preferred embodiment of a sensor system that detects thrombi, plaques and stents by using such a sensor element.

The First Embodiment

Figure 3:
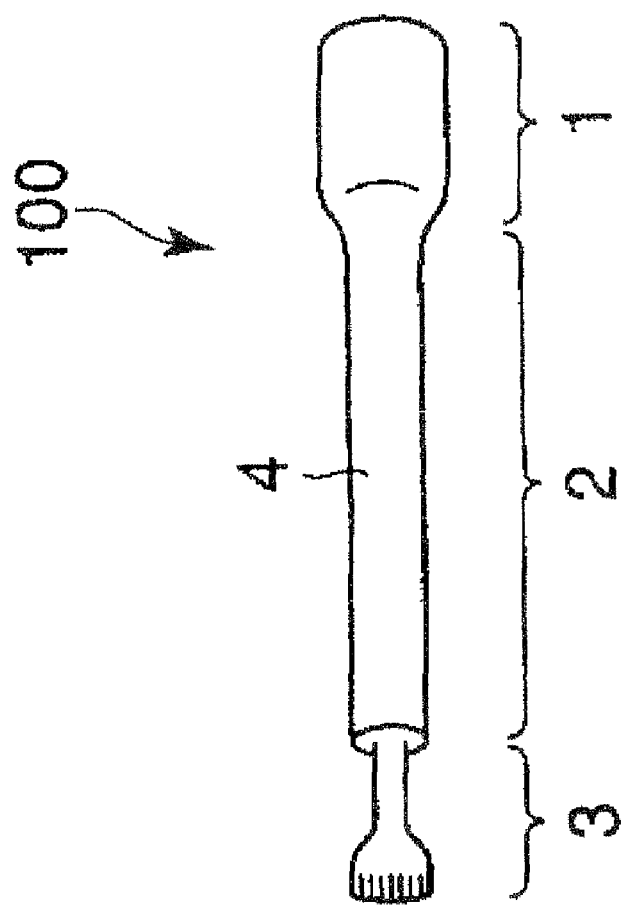
FIG. 3 is an oblique perspective drawing of the outer view of the sensor element 100 in a first embodiment of the present invention.

FIG. 3 is an oblique perspective drawing that shows the outer view of the sensor element 100 regarding the first embodiment of the present invention.

The sensor element 100 includes a sensor portion 1, extension tube portion 2 and contact portion 3. The sensor portion 1 and the extension tube portion 2 are armored with a common insulating pipe 4. For the insulating pipe 4, a thermally shrinkable and biocompatible tube may be used. Smooth and slippery polymers are preferred for the sensor element 100 so that the insertion into blood vessel and the transportation of the sensor element 100 in the blood vessel may be facilitated. For such polymers, for example, HDE (High density poly-Ethylene) and Pebax (a trade mark) are usable. A UV photo polymer, which is strong and can be expanded into thin film, can be used. Pebax is a wide range thermoplastic elastomer which is polyether block amide copolymer and has good mechanical, physical and chemical characteristics and is preferred as a sheath material.

Figure 4:
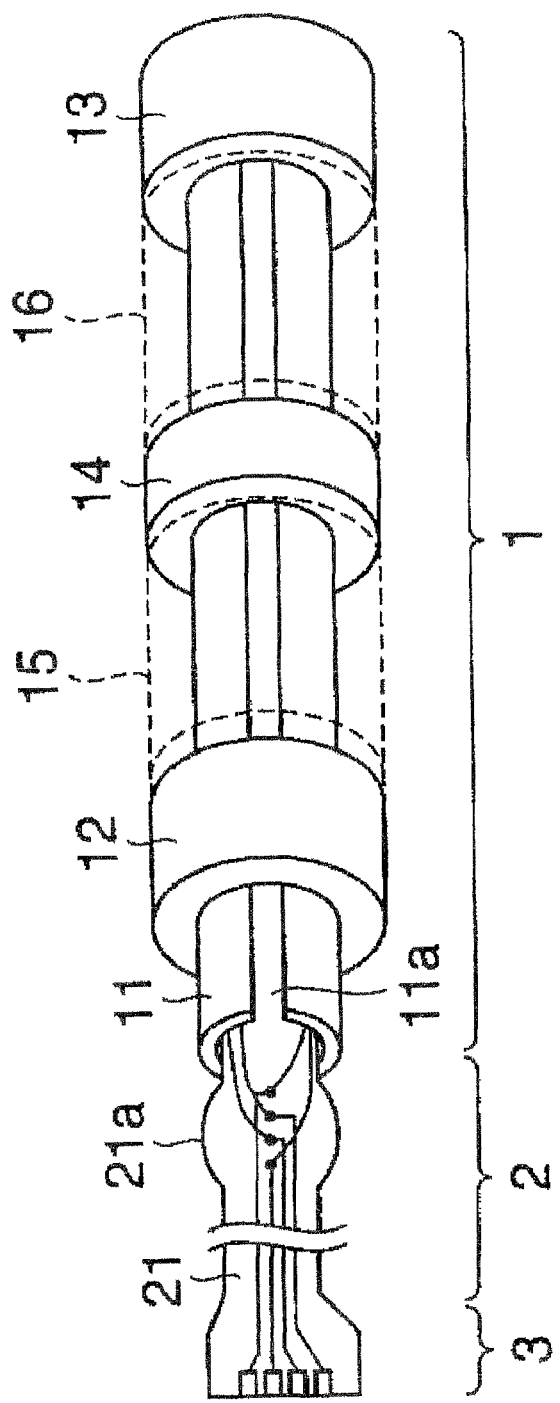
FIG. 4 is an oblique perspective drawing of a structure of the sensor element 100 excluding the insulating pipe 4.

FIG. 4 is an oblique perspective drawing of a structure of the sensor element 100 excluding the insulating pipe 4.

The sensor portion 1 includes a cylinder 11, a signal exciting coil 12, a signal receiving coil 13, a spatially differentiating coil 14 and spacers 15 and 16. A spatially differentiating coil is a differential electrical coil that reduces the induced signal received by a signal receiving coil 13, of which signal is induced by the exciting signal applied to the signal exciting coil 12, with the induced signal that is induced in the differential electrical coil. Each induced signals induced in the signal receiving coil 13 or in the spatially differentiating coil 14 has specific spatial susceptibility around each coil. Therefore, the spatial differentiating coil 14 has electrical characteristics of "spatial differential" that exploits the difference of such spatial susceptibility.

The cylinder 11 is made of a flexible material formed into a cylindrical shape. In addition to mechanical flexibility, the materials used for making the cylinder 11 can preferably keep the cylindrical form even when a certain magnitude of external forces is applied. For such purpose, the following examples are preferably appropriate such as polytetrafluoroethylene (4-fluoride), tetrafluoroethylene-perfluorooctane-alkyl-vinyl-ether copolymer, tetrafluoroethylene-hexafluoropropylene copolymer (4.6 fluoride), tetrafluoroethylene-ethylene copolymer, polyvinylidene-fluoride (2-fluoride), polychlorotrifluoroethylene copolymer (trifluoride), chlorotrifluoroethylene-ethylene copolymer. The cylinder 11 may be made of magnetic or non-magnetic material. The cylinder 11 has an open end at least at one end. A slit 11a is formed along the axis of the cylinder 11 from the open end. The width of the slit 11a is less than the diameter of the inner space of the cylinder 11.

The signal exciting coil 12, the signal receiving coil 13 and the spatially differentiating coil 14 are arranged such that they are wound around the outer surface of the cylinder 11. The signal exciting coil 12, the signal receiving coil 13 and the spatially differentiating coil 14 are separated, and the spatially differentiating coil 14 locates between the signal exciting coil 12 and the signal receiving coil 13.

Figure 5:
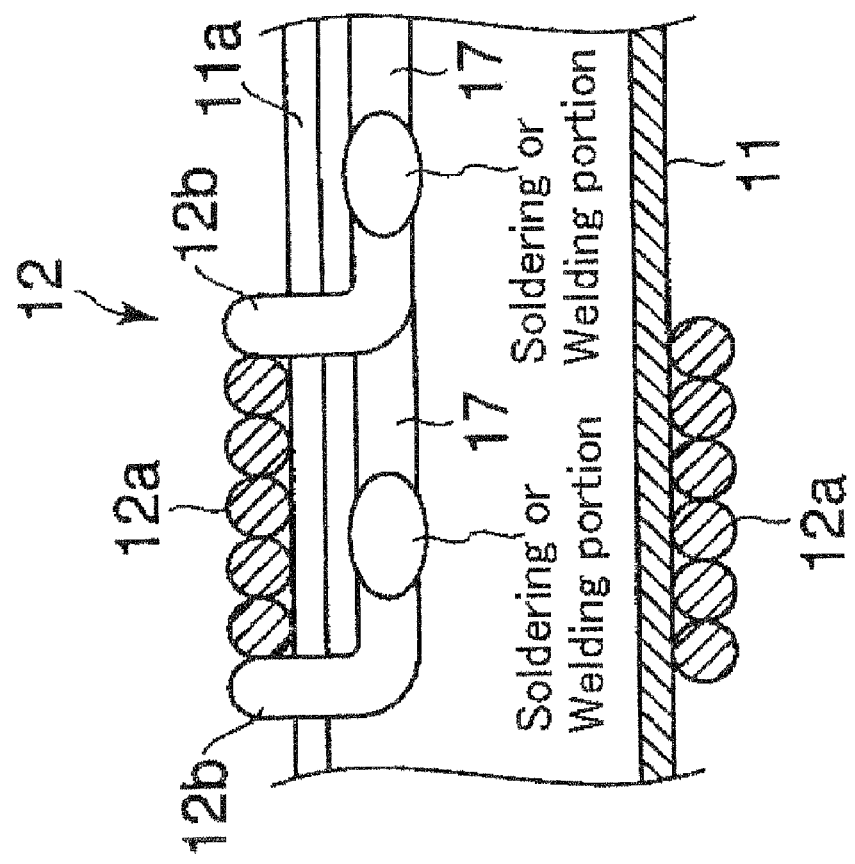
FIG. 5 is a cut away drawing of a cross sectional view which includes the central axis of the cylinder 11 and the slit 11a around the signal exciting coil 12.

FIG. 5 is a cut away drawing that shows the cross sectional view which includes the central axis of the cylinder 11 and the slit 11a around the signal exciting coil 12. The arrangement of the signal exciting coil 12 is constructed in a way that the cylinder 11 has an open end at least one end, and a slit 11a is formed along the central axis of the cylinder 11 in the cylinder 11, wherein the width of the slit is less than the diameter of the inner space of the cylinder 11. The signal exciting coil is a coil element that is formed in a way that the signal exciting coil 12 includes a wound wire portion 12a that comprises one wound wire having one winding direction and two lead portions 12b that are formed at both ends of the wound wire portion 12a wherein the wound wire portion 12a is formed on the surface of the cylinder 11 and the two lead portions 12b are led into the inner space of the cylinder 11 by passing through the slit 11a.

Figure 6:
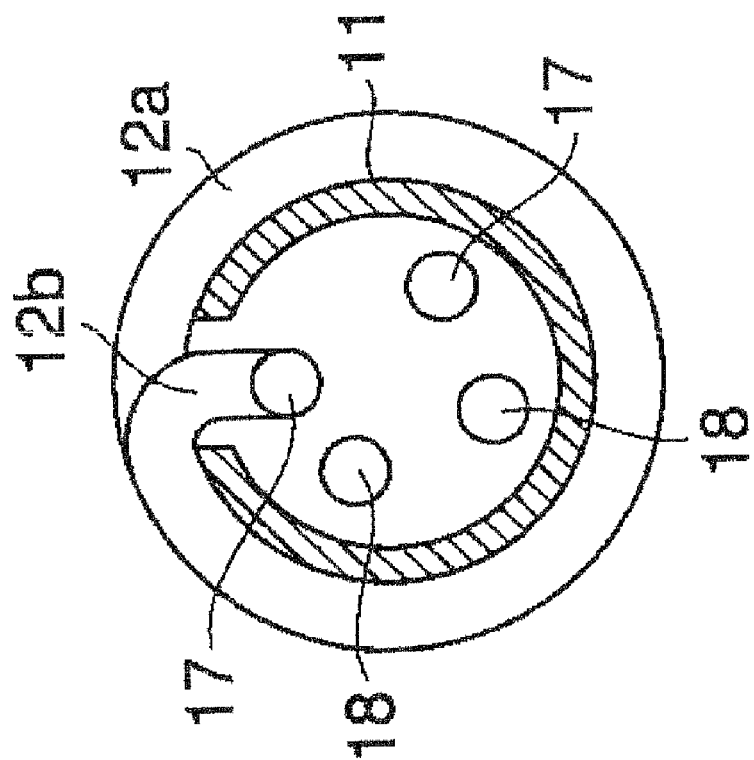
FIG. 6 is a drawing of a cross sectional view of the sensor element that includes the signal exciting coil 12 that is perpendicular to the central axis of the cylinder 11.

FIG. 6 is a drawing of the cross sectional view of the sensor element that includes the signal exciting coil 12 that is perpendicular to the central axis of the cylinder 11.

The lead portions 12b of the signal exciting coil 12 are electrically connected to the electrical wire 17, which is an electrically conducting means (as shown as soldering or welding portions in FIGS. 5 and 7), by means of soldering or welding.

As for a signal exciting coil 12, the present embodiment adopts an independent coil element. The signal exciting coil 12 includes the wound wire portion 12a and two lead portions 12b that are formed at both ends of the wound wire portion 12a. The two lead portions 12b are led into the inner space of the cylinder 11 by passing through the slit 11a. The both end portion of the lead portion 12b are bent to roughly direct to the central axis of the cylinder 11 and welded to the two electrical wires 17.

Figure 7:
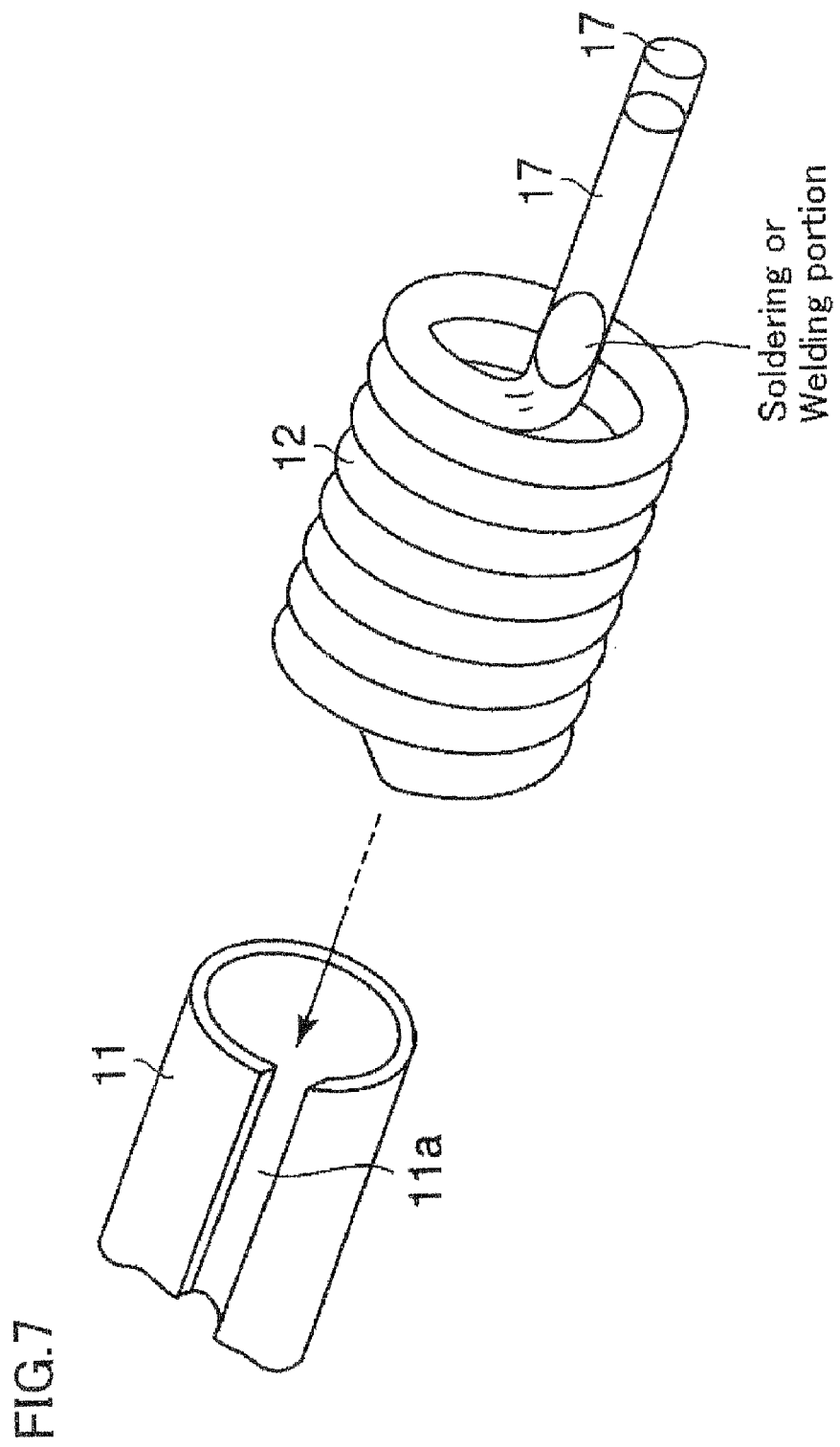
FIG. 7 is a drawing of a process for manufacturing the sensor element 100.

When the sensor element 100 is manufactured, the following process is performed. A copper wire is wound around the outer surface of the cylinder 11 with a slightly larger diameter than that of the outer diameter of the cylinder 11 to form the wound wire portion 12a and the both ends of the copper wire are bent to form the lead portions 12b as described above. Then, electrical wires 17 are welded to the lead portions 12b. As shown in FIG. 7, the signal exciting coil 12 is slid on the outer surface of the cylinder 11 passing through the open end in a way that the both ends of the signal exciting coil 12 are slid in the slit 11a, and electrical wires 17 are worn onto the surface of the cylinder 11.

The two lead portions 12b can be extended to be electrical wires 17.

Figure 8:
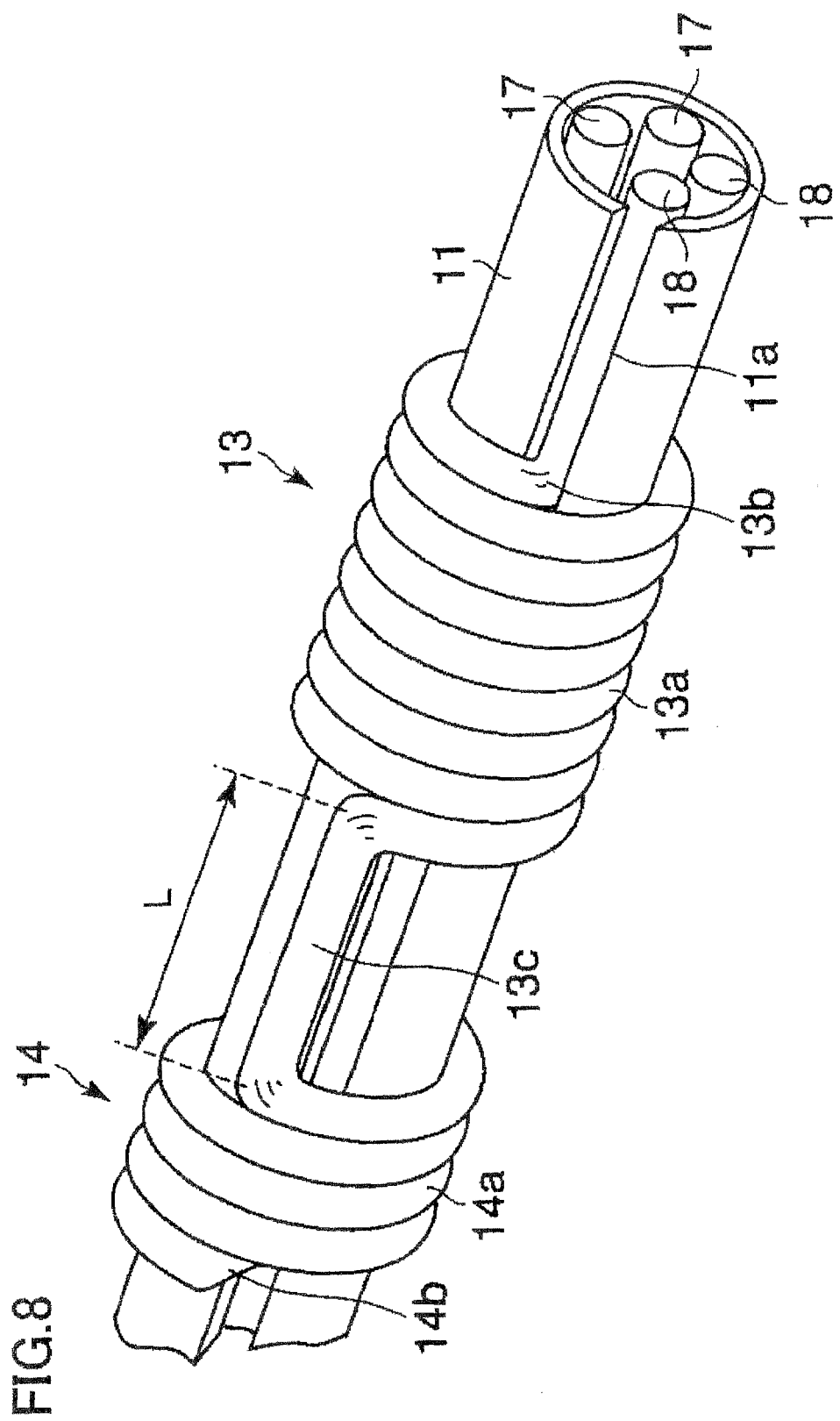
FIG. 8 is an oblique perspective drawing of an over view of the coil elements that include the receiver coil 13 and the spatially differentiating coil 14.

FIG. 8 is an oblique perspective drawing that shows the over view of the coil elements that includes the receiver (i.e., signal receiving) coil 13 and the spatially differentiating coil 14.

In details, the first coil element (not shown in FIG. 8 but exists in the left side of the cylinder 11), which is a signal exciting coil, and the second coil, including the signal receiving coil 13, and the spatially differentiating coil 14 compose a coil element group, wherein the wound wire portion of a first coil element is a wound wire having one winding direction, the wound wire portion of the second coil element comprises another first wound wire having one winding direction and a second wound wire having different winding direction from the one winding direction, wherein the first wound wire and the second wound wire are connected via an electrically connecting portion.

More specifically, a coil element as shown in FIG. 8 is used for the present embodiment for the signal receiving coil 13 and the spatially differentiating coil 14. The wound wire portion 13a, which is the major portion of the signal receiving coil 13, and the wound wire portion 14a, which is the major portion of the spatially differentiating coil 14, are formed in similar manner as the wound wire portion 12a by using a single copper wire. However the central axes of the wound wire portions 13a and 14a are mutually coincident, and the wound wire portions 13a and 14a are formed in separation along with the central axes. The one end of the wound wire portion 13a and the one end of the wound wire portion 14a are bent in a form of lead portion 13b and 14b and are led into the central axis of the cylinder 11, respectively. The other end of the wound wire portion 13a and the other end of the wound wire portion 14a are electrically connected. The wound wire portions 13a and 14a, lead portions 13b and 14b and the electrically connecting portion 13c are formed in a single form with a single copper wire. Of course, the coil elements independently formed may be used for the signal receiving coil 13 and the spatially differentiating coil 14, and another copper wire may be formed into the signal exciting coil 12. The signal receiving coil 13 and the spatially differentiating coil 14 are wound in different winding direction so that the signal received by the signal receiving coil 13 is differentially induced against the signal received by the spatially differentiating coil 14. The wound turn of the spatially differentiating coil 14 is less in number of turns than that of the signal receiving coil 13, and therefore the length of the spatially differentiating coil 14 is shorter than that of the signal receiving coil 13.

The lead portions 13b and 14b may be led into the inner space of the cylinder 11 through slit 11a like as the lead portion 12b of the signal exciting coil 12 and welded to the two electrical wires 18 that are the electrically conducting means.

In manufacturing the sensor element 100, the signal receiving coil 13 and the spatial coil 14 are wound onto the surface of the cylinder 11 like as the manufacturing process for the signal exciting coil 12.

Since the sensor element 100 needs to be moved in the blood vessels, it has to be very small in the physical size. However, the above manufacturing process for the sensor element 100 is done in a simple process, and, therefore, it is possible to easily and durably be assembled, even when each of the coil elements is small.

The spacers 15 and 16, shown in FIG. 4, are respectively mounted to the cylinder 11 between the signal exciting coil 12 and the spatially differentiating coil 14 and between the signal receiving coil 13 and the spatially differentiating coil 14, so that the sensor portion 1 has the surface that is the outer surface of the insulating pipe 4 and that is a smooth single cylinder surface. However, the spacers 15 and 16 are shown by broken lines in FIG. 4 in order to clarify the spatial position of the cylinder 11 and the exiting coil 12 and that of the signal receiving coil 13 and the spatially differentiating coil 14. As for the cylinder 11, the signal receiving coil 13 and the spatially differentiating coil 14 are all drawn with solid lines, even for the portion hidden by the spacers 15 and 16. As shown in FIG. 4, a flexible printed circuit board (hereinafter PCB) 21 that functions as electrical cables is set in side of the extension tube portion 2. The flexible PCB 21 has one end that is inserted into the inner space of the cylinder 11 through the open end of the cylinder 11. The other open end of the cylinder 11 may be left as is or may have a insulating rod and globe that have the same outer dimensions as the inner diameter of the cylinder 11, respectively, in order to maintain the circle shape for the cross section of the cylinder 11. The flexible PCB 21 has a stopper portion 21a, which has a width larger than the inner diameter of the cylinder 11. The stopper portion 21a prevents the flexible PCB 21 from going into the inner space of the cylinder 11 more than necessary. In the flexible PCB 21, more than four wire patterns are formed up to the portion close to the other end of the flexible PCB 21 than that of the stopper portion 21a. To these four wire patterns, a set of two electrical wires 17 and another set of two electrical wires 18 are soldered at the portion near the stopper portion 21a. In other words, two-wire pattern of such four-wire pattern are used for the propagation of the exciting signal that excites the signal exciting coil 12, and another set of two-wire pattern is used for the propagation of the receiving signal that is received by the spatially differentiating coil 14. The portion formed close to the stopper portion 21a in the flexible PCB 21 has land portions to which electrical wires 17 and 18 are soldered.

The end portion of the flexible PCB 21 is used for the contact portion 3 which is formed such that the thickness and the width of the flexible PCB 21 are conformed to be fitted to the connector. The contact portion 3 has a plurality of electrical contacts that contact with those formed in the connector. At least four patterned wires are formed on the flexible PCB 21, and they connect to the contacts of the contact portion 3.

For the signal propagation in the extension tube portion 2, another type of cables which are built-in the extension tube portion 2 may be used instead of the flexible PCB 21. As for such another type of cables, well-known coaxial cables, for example, can be used. When a cable which includes plurality of wires, each of the electrical wires 17 and 18 is directly connected to each of such plurality of wires. By the plurality of wires being directly connected to the lead portion 12b, 13b and 14b, these wires are commonly used as the electrical wires 17 and 18. When coaxial cables are used, a plug is preferably attached instead of the contact portion 3. The lead portions 12b, 13b and 14b are preferably not to be set inner space of the cylinder 11 but are preferably led out to the outside of the inner space of the cylinder 11.

Figure 9:
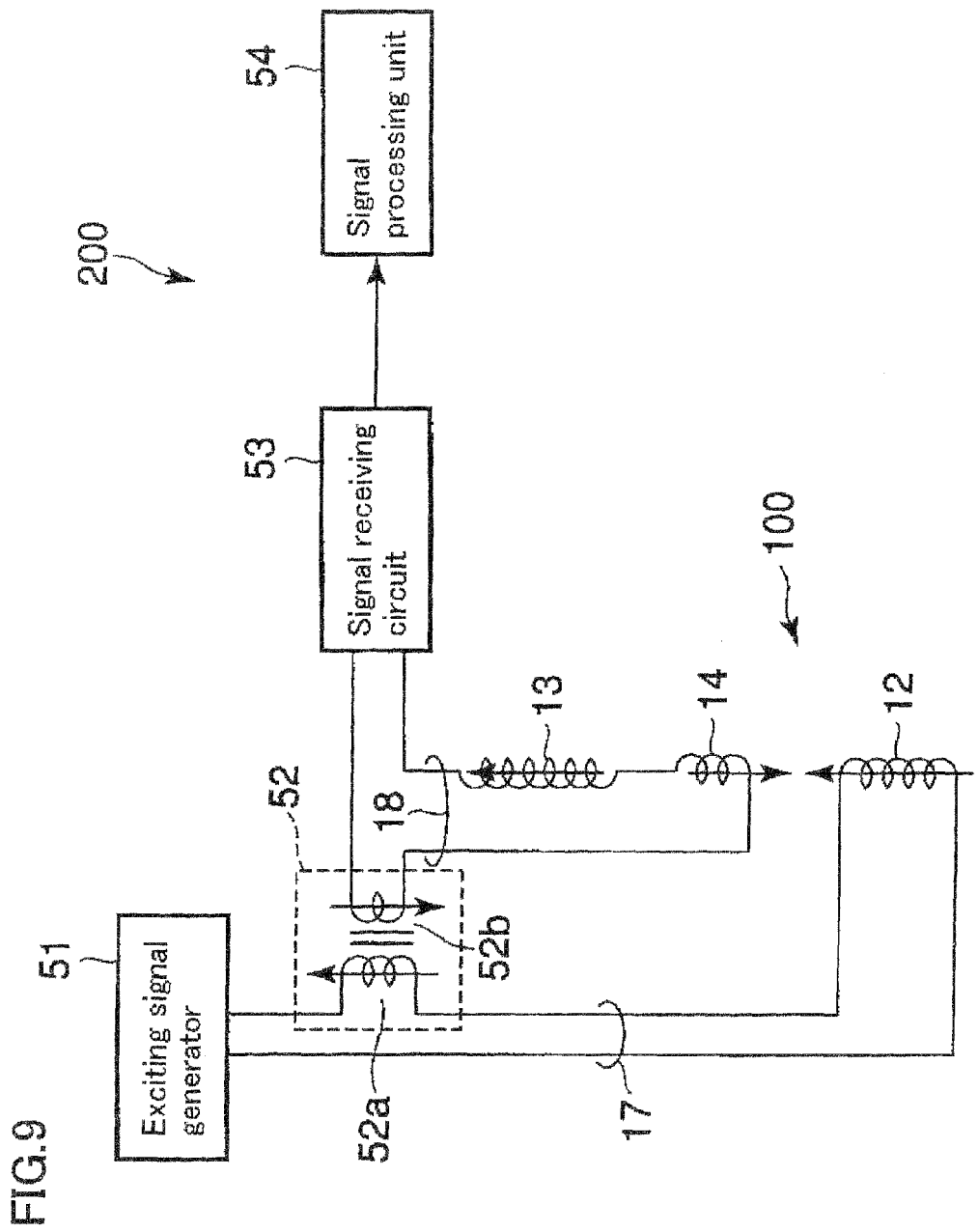
FIG. 9 is a circuit diagram of the sensor system 200 that uses the sensor element 100.

FIG. 9 is a drawing that shows the structure of the sensor system 200 that uses the sensor element 100 configured as described above. The arrow written aside each coil denotes the polarity of the coil coupling. That is, if the arrow directions of a coil shows are in reverse orientation each other, then the induced signal is in differential relation, and if the arrows are in same orientation as each other, then the induced signal is in summation.

The sensor system 200 as shown in FIG. 9 is constructed as follows. The sensor portion 1 (not shown in FIG. 9) includes the sensor element 100, which includes the second coil element that further includes the first coil element, which is the signal exciting coil 12, and the second coil element, which consists of the signal receiving coil 13 and the spatially differentiating coil 14. The wound wire portion of the first coil element is a wound wire having one winding direction and forms an signal exciting coil 12. The wound wire portion of the second coil element form a signal receiving coil 13 with the first wound wire having one winding direction and a spatially differentiating coil 14 with the second wound wire having the other winding direction. Moreover, the signal receiving coil 13 and the spatially differentiating coil 14 are connected in series. Specifically, they are electrically connected via an electrically connecting portion 13c as shown in FIG. 8. The sensor system 200 includes an exciting signal generator 51, an external differential transformer 52 that is a signal reducing means and signal receiving circuit 53. The Sensor system 200 is configured as described hereinafter. That is, the sensor system 200 includes the first coil element that is the signal exciting coil 12 functioning as an electric coil. The sensor system 200 is equipped with the exciting signal generator 51 that generates an exciting signal which is sent through the pair of the electrical wires 17 and the second coil element that is the signal receiving coil 13 and the spatially differentiating coil 14. The sensor system 200 is equipped with the signal receiving circuit 53 that receives the induced signal induced by the signal receiving coil 13 and the spatially differentiating coil 14 trough the pair of the electrical wire 18. The signal exciting coil 12 is connected to the exciting signal generator 51 through the primary coil 52a of the differential transformer 52, and the signal receiving coil 13 and the spatially differentiating coil 14 are connected in series and connected to the signal receiving circuit 53 through the secondary coil 52b of the external differential transformer 52.

The sensor element 100 is installed in the sensor system 200 by setting the contact portion 3 (as shown in FIG. 4) in the connector that is connected to the exciting signal generator 51, the external differential transformer 52 and the receiving circuit 53.

The exiting signal generator 51 supplies AC exciting signal to the signal exciting coil 12.

One terminal of the primary coil 52a of the external differential transformer 52 is connected to the exciting signal generator 51 and the other terminal is connected to a terminal of the signal exciting coil 12. One terminal of the secondary coil 52b of the external differential transformer 52 is connected to the signal receiving circuit 53 and the other terminal is connected to one terminal of the spatially differentiating coil 14. The winding direction of the secondary coil 52b is reverse of that of the signal receiving coil 13.

One terminal of the signal receiving coil 13 and one terminal of the secondary coil 52b are connected to the signal receiving circuit 53. As the results, a circuitry that is the signal receiving circuit 53 to which the signal receiving coil 13, the spatially differentiating coil 14 and the secondary coil 52b are connected in series is completely configured. The signal receiving circuit 53 receives the induced signal by this circuitry.

In such a configuration, the received signal at the signal receiving coil 13 is differentiated with those received by the spatially differentiating coil 14 and induced at the secondary coil 52b of the external differential transformer 52. In other words, the spatially differentiating coil 14 and the secondary coil 52b of the external differential transformer 52 have reversed polarities compared to the polarity of the signal receiving coil 13 in the normal polarity. The primary transformer coil 52a of the external differential transformer 52 and the signal exciting coil 12 have the same polarity.

The present sensor system 200 equips with a signal processing system 54 in addition to the signal receiving circuit 53.

In other words, the signal processing system 54 is a judgment unit that functions in accordance with the signal received by the signal receiving circuit 53 to judge the physical parameters of the substance that exists around the sensor element 100. The function of the processing system 54 is explained in the following description. The processing system 54 is to judge the existence of at least one of the plaques or thrombi formed or stents inserted in the blood vessels.

(Insertion of the Sensor Element 100 into Blood Vessels)

The sensor system 200 is used in which the sensor element 100 is inserted into the blood vessel of a patient. The central part of structure of the sensor element 100 is the cylinder 11 that has a slit 11a as shown in FIG. 4. However, the width of the slit 11a is relatively small and therefore the cylinder 11 has practically a cylinder shape, while the sensor element 100 with the slit 11a in the cylinder 11 is guaranteed to have flexibility so that the sensor element 100 can be easily moved in the blood vessels. Since the cylinder 11 has practically a cylinder shape, the thickness of the cylinder 11 can be uniform and less stress is concentrated. Therefore, the cylinder 11 can avoid being easily broken, even if the sensor element 11 is bent in the curvatures of the blood vessels. The dispersion of the stress in the cylinder 11 can accept the thinner pipe of the cylinder 11 that leads to reduce the outer diameter of the sensor element 100 so that the sensor element 100 can be inserted into a thin blood vessels.

(Fundamental Operation)

When the exciting signal generated by the exciting signal generator 51 is supplied to the signal exciting coil 12, a signal is induced in the signal receiving coil 13. It is well known that the judgment whether the surrounding substances around the sensor element 100 are normal artery cells or vessels cells, thrombi, plaques or stents or the measurement of the diameters of such surrounding substances can be done from the principle of ILS. That is, the induced current in the surrounding substance around the sensor element 100 varies the magnitude and the phase due to the distance for the substance from the signal exciting coil 12. The magnitude and the phase of the induced signal in the coil 13 varies with the induced current in the substance around the sensor element 100. Therefore, it is possible to obtain the separation distance of the substance from the signal exciting coil 12 by means of the signal processing system 54 that evaluates the signal induced in the signal receiving coil 13 after it is received by the signal receiving circuit 53. The substances, such as blood, normal blood vessel cells, thrombi, plaques and stents, have different electrical resistance. According to the differences of the electrical resistance, it is possible to judge the substance close to the sensor element 100 normal blood vessel cells, thrombi, plaques or stents. By using the distance which is specified when thrombus or plaque is detected around the sensor element 100, it is possible to know the diameter of the angio stenosis or infarction part due to the thrombi or plaques. When stents are detected around the sensor element 100, it is possible to know the expanded diameters of the stents (which are inner diameters of the stents).

(External Differentiating Operation)

Figure 10:
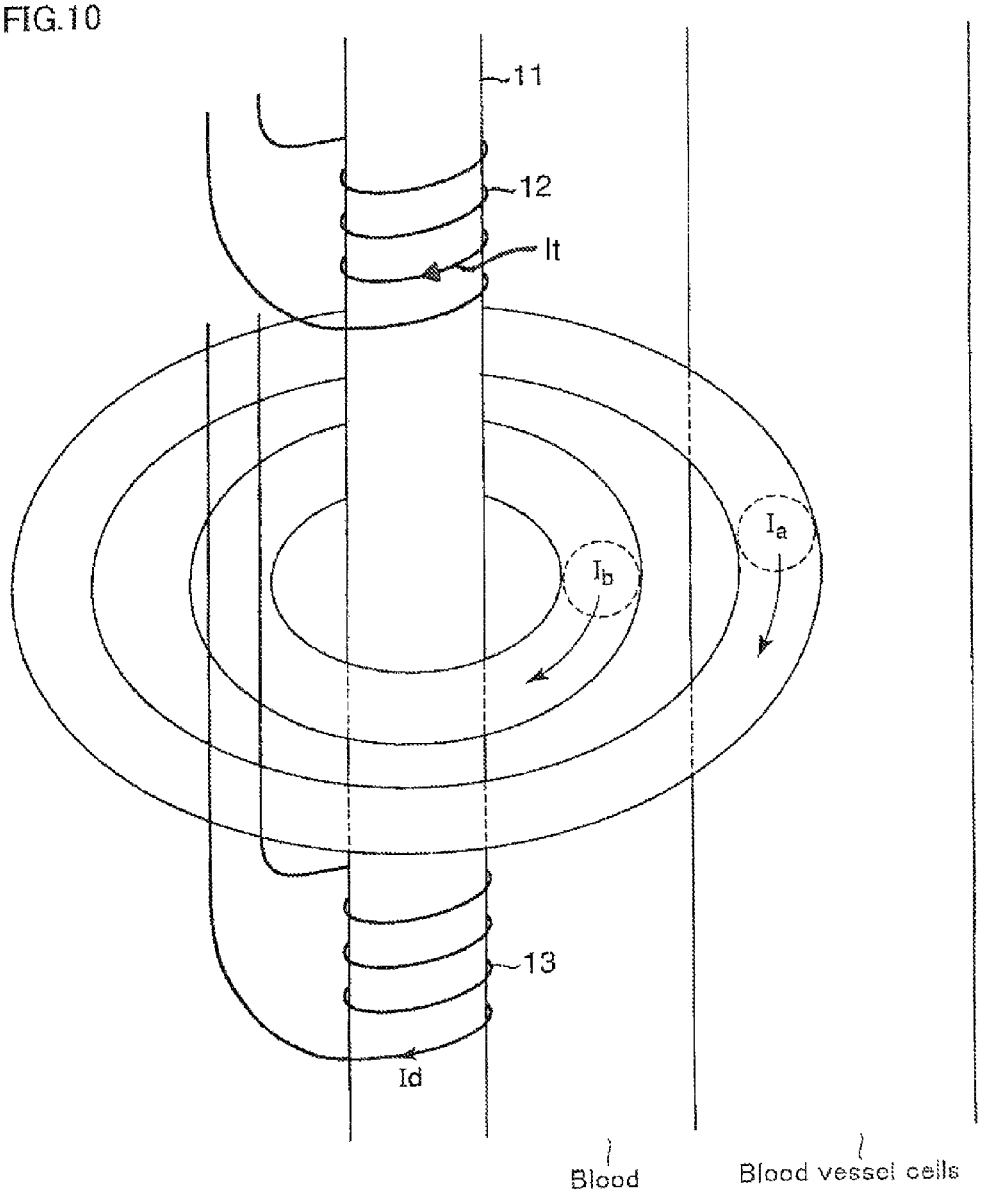
FIG. 10 shows a schematic of the blood vessel current Ia and the blood current Ib induced in the blood vessel.

When the signal exciting coil 12 is excited, the induced current Id is directly induced in the signal receiving coil 13, as shown in FIG. 10. Inside the blood vessel (that is, in the blood), the induced blood current Ib is induced as shown in FIG. 10. The induced angio current Ia is induced in the blood vessel cell. Therefore, the induced voltage Va in the signal receiving coil 13 responds to the summation of the current as Id+Ib+Ia. The important element for the analysis in the signal processing system 54 is the induced angio current Ia. However, the largest induced current is Id among the induced currents Id, Ia and Ib. This is the cause of reducing the sensitivity of the measurement.

To solve this problem, the sensor system 200 is equipped with the external differential transformer 52. The ratio of the coil wound number of the primary coil and of the secondary coil of the external differential transformer 52 is appropriately determined in response to the coupling rate of the direct coupling between the signal exciting coil 12 and the signal receiving coil 13 so that the induced voltage Va', which has a reverse polarity to Va, is generated responding to the induced current Id in the secondary coil 52b through the primary coil 52a as the exciting coil 12 being driven by the exciting signal. By such induction of the signals, the receiving circuit 53 receives Va−Va' which implies the receiving circuit 53 receives the signal that corresponds to (Id+Ib+Ia)−Id=Ib+Ia.

As the results, the signal receiving circuit 53 can only receive the signal resulting from the induced current in the substance existing around the sensor element 100 without the influence of the large current caused by the direct coupling between the signal exciting coil 12 and the signal receiving coil 13 so that the improvement of the sensitivity of the detecting the substance can be achieved. Since the induced current Id is proportional to the current It of the exciting signal, the differential operation obtained by using the external differential transformer 52, as explained above, does not become affected by the instability of the exciting signal generator where all signals are reference to the exciting signal.

For the external differential transformer 52, it is also possible to use a well-known transformer that has a function to vary the coupling ratio between the primary coil 52a and the secondary coil 52b. By using such a transformer as an external differential transformer 52, it is possible to minimize the influence of the direct coupling between the signal exciting coil 12 and the signal receiving coil 13 by appropriately adjusting such coupling ratio of the external differential transformer 52.

Once the induced voltage Va−Va' is equal to zero, such as when the sensor element 100 is placed in the air by adjusting or setting the coupling ratio of the external differential transformer 52, the sensor element 100 is then inserted into the blood vessel. The induced voltage Va−Va'(=Va0) becomes non-zero. The induced voltage Va0 corresponds to the value of the conductivity of the blood vessel. When thrombi, stents or plaques exists, the detection of Va−Va'(=Vm) for the current signal Ia for each of these substances can specify the existence of thrombi, stents or plaques based on the voltage value of Vm−Va0. For the measurement of stent diameters, large value of Vm−Va0 is used because the large conductivity of the stent material that is a metal. Since the value Vm−Va0 is a differential signal, the phase of such differential signals is reversed for the case of existence of a stent and for the case of the existence of thrombus or plaque. For the actual usage, Vm−Va0 is measured for various diameters of the stents beforehand and such data are kept for the subsequent measurement. Then the diameter of the stent being expanded in the blood vessel is reversely computed by using such data. The signal processing unit 54 has such function of the reverse computation.

The measurement of above induced voltage due to the induced current is carried out synchronously with detecting the voltage signal in the phase of the current which is the source of the induction phenomena.

(Spatial Differential Operation)

The sensor element 100 is transported and moves in the channel of blood flow in the blood vessel. The blood is closer to the sensor element 100 than blood vessel cells, thrombi, plaques or stents. Accordingly, the induced current Ib is larger than Ia, and this reduces the sensitivity of the measurement.

It is necessary to use fine copper wire for the signal exciting coil 12 and the signal receiving coil 13 for the purpose to make the sensor element 100 small enough but the electrical resistances of these coils become large. In order to increase the total current of the coils for compensation for such large resistance, we provide more coil wound number by winding more coil. Accordingly, the induced current by the signal exciting coil 12 increases and the voltage induced in the coil 13 becomes large, since the induced current and the induced voltage are proportional to the coil wound number. Therefore, the measurement becomes easier when the coil wound number of the coil 13 is increased. However, the length of the coils along the central axis (called "z-axis" hereinafter) of the cylinder 11 becomes large, in order to not make the outer diameters of the exiting coil 12 and signal receiving coil 13 large but increase the coil wound number. This degrades the resolution of detection of substances along z-axis.

In order to solve this problem, the present embodiment equips with the spatially differentiating coil 14.

The spatially differentiating coil 14 locates closer to the signal receiving coil 13 than to the signal exciting coil 12. Therefore, the spatially differentiating coil 14 has high sensitivity to the substance which locates closer to the sensor element 100 than to the signal receiving coil 13. In other words, the induced current of the spatially differentiating coil 14 is more influenced by the induced current Ib than by the induced current of the signal receiving coil 13. On the other hand, the wound wire direction of the signal receiving coil 13 and that of the spatially differentiating coil 14 are mutually reversed. Therefore the induced current in the spatially differentiating coil 14 and that in the signal receiving coil 13 are reversed polarities (or reverse phase). Since the coil wound number of the signal receiving coil 13 is smaller than the coil wound number of the spatially differentiating coil 14, the absolute sensitivity of the spatially differentiating coil 14 is smaller. Due to this fact, the signal receiving circuit 53 obtains the improvement in sensitivity, because the signal that has less influence of the induced current Ib is generated by the induced current in the coil 13 being subtracted with the induced current in the spatially differentiating coil 14. That is, the signal differentiated by the induced current by signal receiving coil 13 and that by the spatially differentiating coil 14 is received.

Figure 11:
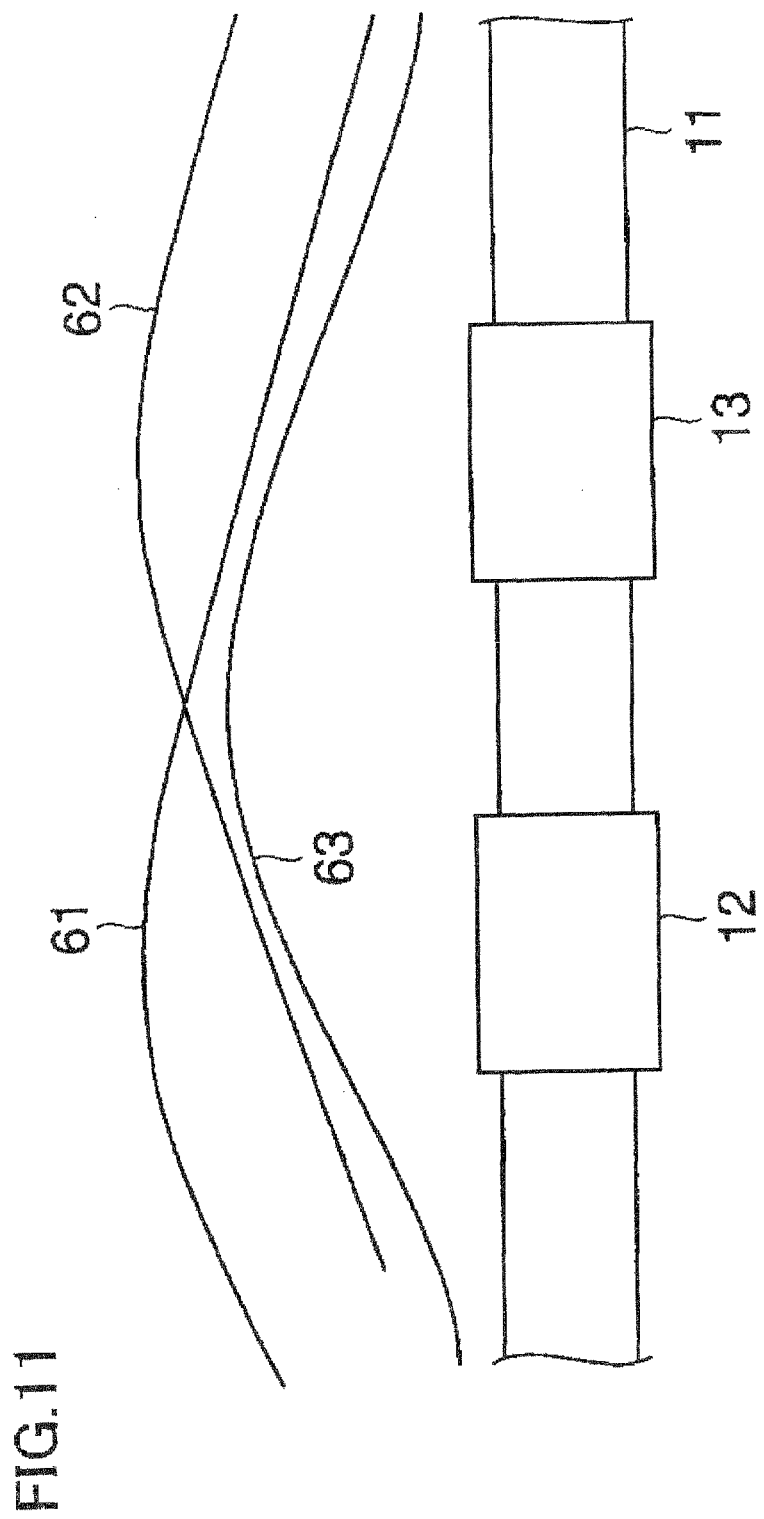
FIG. 11 shows the spatial measurement characteristics along z-axis for the case when the sensor element 100 equips with no spatially differentiating coil 14.

FIG. 11 shows the spatial measurement characteristics along z-axis for the case where the sensor element 100 is equipped with no spatially differentiating coil 14.

When no spatially differentiating coil 14 is present, the spatial measurement characteristics 63 as shown in FIG. 11 is obtained as a composition of the spatial excitement characteristics 61 of the signal exciting coil 12 and the spatial susceptibility 62 of the signal receiving coil 13. When the lengths of z-axis direction regarding the signal exciting coil 12 and the signal receiving coil 13 become large, the spatial excitement characteristics 61 and the spatial susceptibility 62 have more gradual curve against z-axis, and the spatial measurement characteristics becomes a gentle curve, and the resolution of detection of substances along z-axis becomes degraded as discussed before.

Figure 12A:
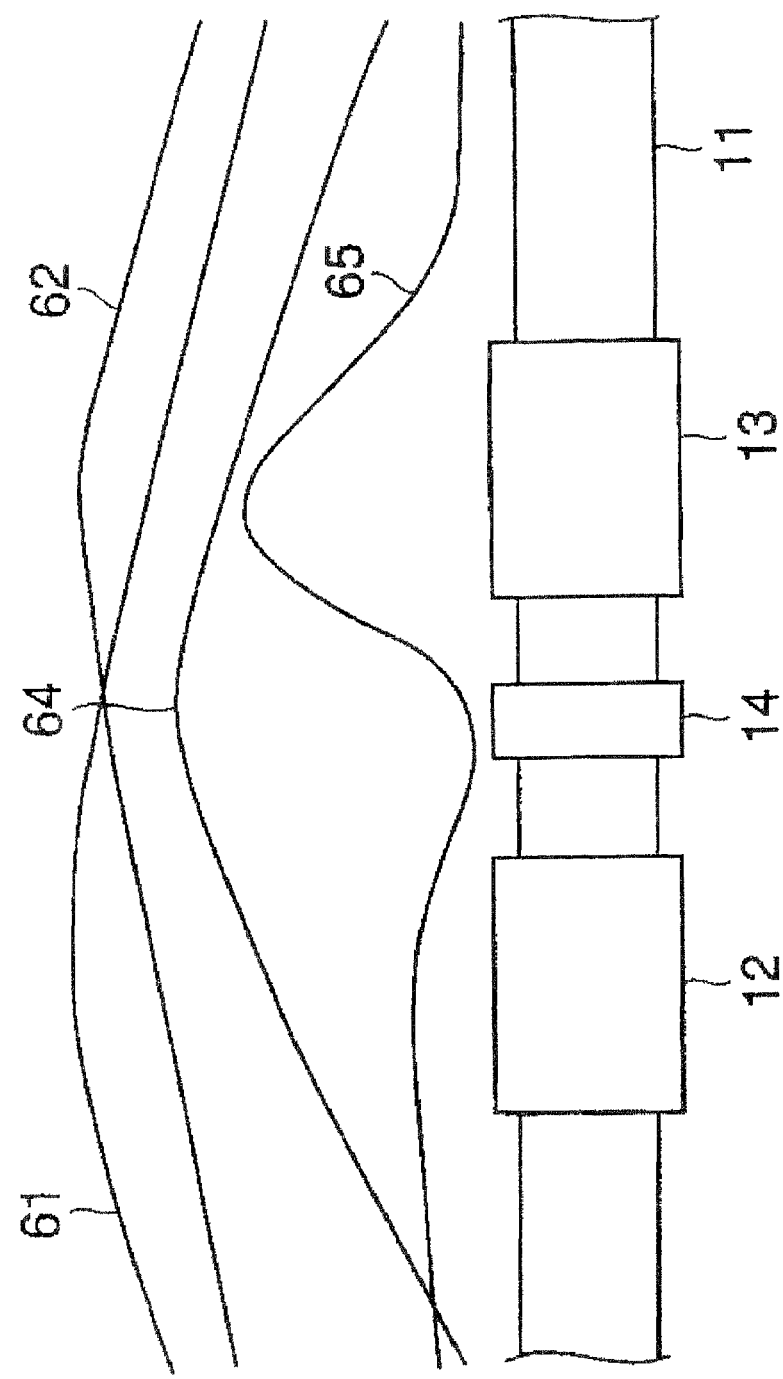
FIG. 12A shows characteristics of the spatial susceptibility of the sensor element 100.

The spatially differentiating coil 14 has the spatial susceptibility 64 as shown in FIG. 12A. The length of the spatially differentiating coil 14 along z-axis is smaller than that of the signal receiving coil 13. Therefore, the curve of the spatial susceptibility 64 is steeper than that of the spatial susceptibility 62. The peak of the spatial susceptance characteristic 64 is between the peak of the spatial excitement characteristics 61 and that of the spatial suscpetance characteristics 62. The induced current in the spatially differentiating coil 14 has the reverse polarity against the induced current in the signal receiving coil 13. Therefore the spatial measurement characteristics of the sensor element 100 is obtained as the spatial measurement characteristics 65 as shown in FIG. 12A, which is the composition of the spatial excitement characteristics 61, spatial suscpetance characteristics 62 and the spatial susceptibility 64. The curve of the spatial measurement characteristics 65 is steeper than that of the spatial measurement characteristics 63. Therefore the spatial resolution along z-axis has been much improved by this spatial susceptibility 65.

The spatial measurement characteristics of the sensor element 100 vary with the relative position to the signal receiving coil 13 and the spatially differentiating coil 14. In order to suppress the deviation of the spatial measurement characteristics of the sensor elements 100 in the manufacturing process, the relative position between the signal receiving coil 13 and the spatially differentiating coil 14 has to be precisely manufactured to be equal among the sensor elements 100. However, the sensor element 100 is manufactured with a single copper wire that is formed into the signal receiving coil 13 and the spatially differentiating coil 14 in a single assembly. Therefore, it is possible to obtain the consistency of the mutual position between the signal receiving coil 13 and the spatially differentiating coil 14 by keeping the length L as shown in FIG. 8 constant. Since the length L is the length of the electrically connecting portion 13c, it is easier to keep this length consistent than to adjust the separation length of the signal receiving coil 13 and the spatially differentiating coil 14, which are independently made, to be constant. Therefore, it is possible to suppress the deviation of the spatial measurement characteristics in z-plane among the plurality of sensor elements 100.

(Exchange of the Sensor Element 100)

Since the sensor element 100 is to be inserted into the blood vessels, it is preferred to be used only one time from a hygienic standpoint. The sensor element 100 in the present embodiment has a contact portion 3 at the end terminal by which the sensor element 100 is electrically connected to the exciting signal generator 51, the external differential transformer 52 and the signal receiving circuit 53 connect to this contact portion 3 to the connector which is connected to the exciting signal generator 51, the external differential transformer 52 and the signal receiving circuit 53.

The sensor element 100 uses the end of the flexible PCB 21 for the contact portion 3. Hence, the manufacturing of the sensor element 100 is easier than the case when the cable and the connector are independently made, and connected and the cost of parts can be reduced.

Figure 12B:
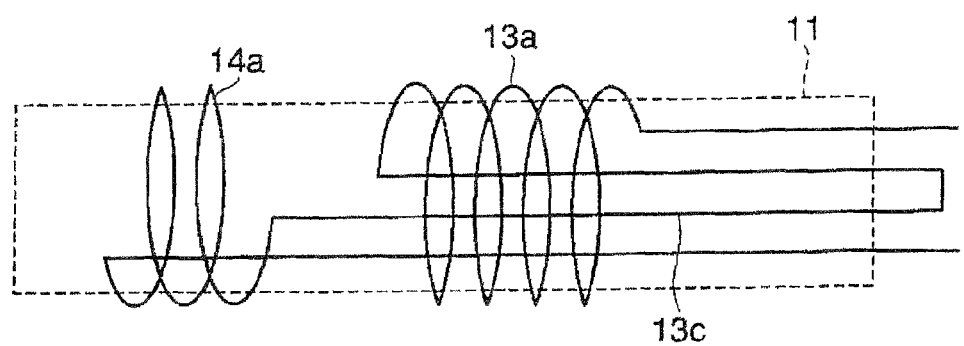
FIG. 12B is a drawing of a variation of the electrical connection of the signal receiving coil 13 and the spatially differentiating coil 14.

The present embodiment can be modified into other various embodiments as explained below. That is, the wound wire portions 13a and 14a are connected in the inner space of the cylinder 11. As shown in FIG. 12B, the middle portion of the electrically connecting portion 13c that connects one end of the wound wire portion 13a to one end of the wound wire portion 14a is led out from the open end of the cylinder 11, and these wound wire portions 13a and 14a are electrically connected outside of the cylinder 11.

The Second Embodiment

Figure 13:
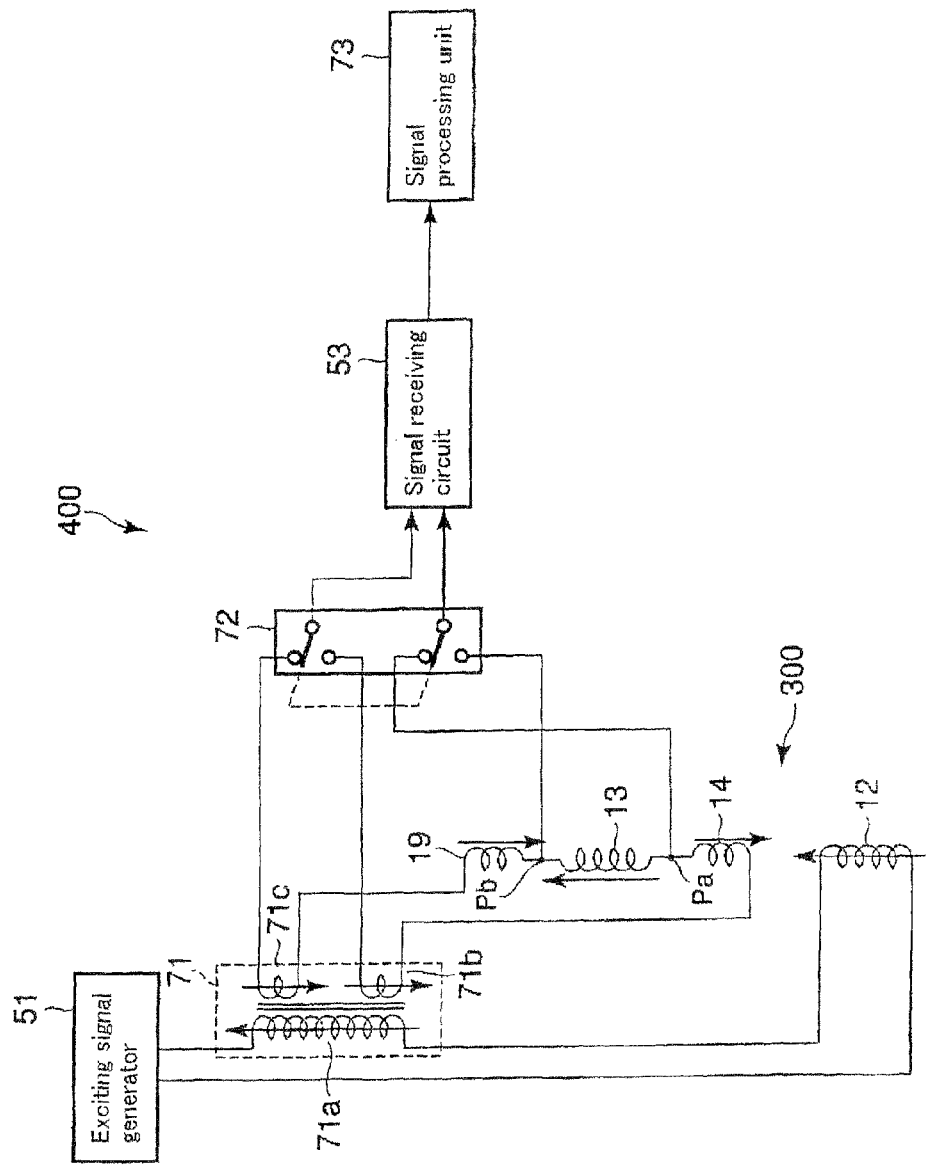
FIG. 13 shows a circuit diagram of a composition of the sensor system 400 which utilizes the sensor element 300.

FIG. 13 shows a composition of the sensor system 400 which utilizes the sensor element 300 that has been modified as explained above. The same numerical labels and alphabets are used in FIG. 13 as the numerical labels and alphabets used in FIG. 9 when denoting the same portion, element, parts and components, and further detailed explanations have been omitted in order to avoid redundant explanation.

The sensor system 400 is equipped with a sensor element 300, an exciting signal generator 51, a signal receiving circuit 53, an external differential transformer 71 that is a signal reducing means, a selector switch 72 that is a signal selector and a signal processing system 73. In other words, the sensor system 400 is equipped with a sensor element 300, an external differential transformer 71 and a signal processing system 73 and additionally a selector switch 72, instead of the sensor element 100 that is a part of the sensor system 200, the external differential transformer 52 and the signal processing system 54 as shown in FIG. 9.

The sensor element 300 is an electrical coil which is composed with the sensor element 100 and a spatially differentiating coil 19 further added. The spatially differentiating coil 19 is aligned in the reverse side of the signal receiving coil 13 against the spatially differentiating coil 14. The spatially differentiating coil 19 is linked to the signal receiving coil 13 in the same manner as the spatially differentiating coil 14, which is linked to the signal receiving coil 13, at a location adjacent to the signal receiving coil 13.

The sensor element 300 further includes two lead portions, one of which is connected to an electrically connecting portion formed between the wound wire portion of the signal receiving coil 13 and that of the spatially differentiating coil 14 and the other of which is connected to an electrically connecting portion formed between the wound wire portion of the signal receiving coil 13 and that of the spatially differentiating coil 19. These two lead portions are led into the inner space of the cylinder 11 through the slit 11a.

The primary coil 71a of the externally differentiating transformer 71 is connected to the exciting signal generator 51 at one terminal and to one end of the signal exciting coil 12 at the other terminal. The first of the secondary coil 71b of the externally differentiating transformer 71 is connected to the selector switch 72 at the one terminal and to the one end of the spatially differentiating coil 14. The second of the secondary coil 71c of the external differential transformer 71 is connected to the selector switch 72 at the one terminal and to the one end of the spatially differentiating coil 19. The wound direction of the secondary coil 71b and 71c is reverse to the wound direction of the signal receiving coil 13.

To the selector switch 72, the electrically connecting point Pa between the signal receiving coil 13 and the spatially differentiating coil 14 and the electrically connecting point Pb between the signal receiving coil 13 and the spatially differentiating coil 19 are connected other than the one terminal of the first of the secondary coil 71b and the one terminal of the second of the secondary coil 71c. These connections are made by electrically connecting the electrically connecting portions that correspond to the electrically connecting points Pa and Pb, to the terminals of the selector switch with two electrical wires as described above in a similarity to the connection with two electrical wires 18. The selector switch 72 selectively configures a first connection state and a second connection state. In the case of the first connection state, one terminal of the first primary coil 71b and the electrically connecting point Pb are connected to the signal receiving circuit 53. In the case of the second connection states, one terminal of the second primary coil 71c and the electrically connecting point Pa are connected to the signal receiving circuit 53.

The signal processing unit 73 detects the thrombi, plaques and stents and specifies the diameters of the stents by analyzing the signal received by the signal receiving circuit 53 in the first connection state and then in the second connection state, and then detects the thrombi, plaques and stents or specifies the diameters of the stents.

For the first connection state, a circuitry similar to the sensor system 200 is configured. On the other hand, a circuitry that uses the spatially differentiating coil 19 instead of the spatially differentiating coil 14 is configured for the second connection state. The circuit configured for the second connection state is electrically equivalent to the circuit configured in the first connection state. However, the spatial susceptibility of the spatially differentiating coil 19 is different from that of the spatially differentiating coil 14, since the position of the spatially differentiating coil 19 is different to that of the spatially differentiating coil 14.

Since the spatial susceptibilities of spatially differentiating coils 14 and 19 are different, the sensor element 300 has different spatial measurement characteristics for the first connection state from that for the second connection state.

Figure 14:
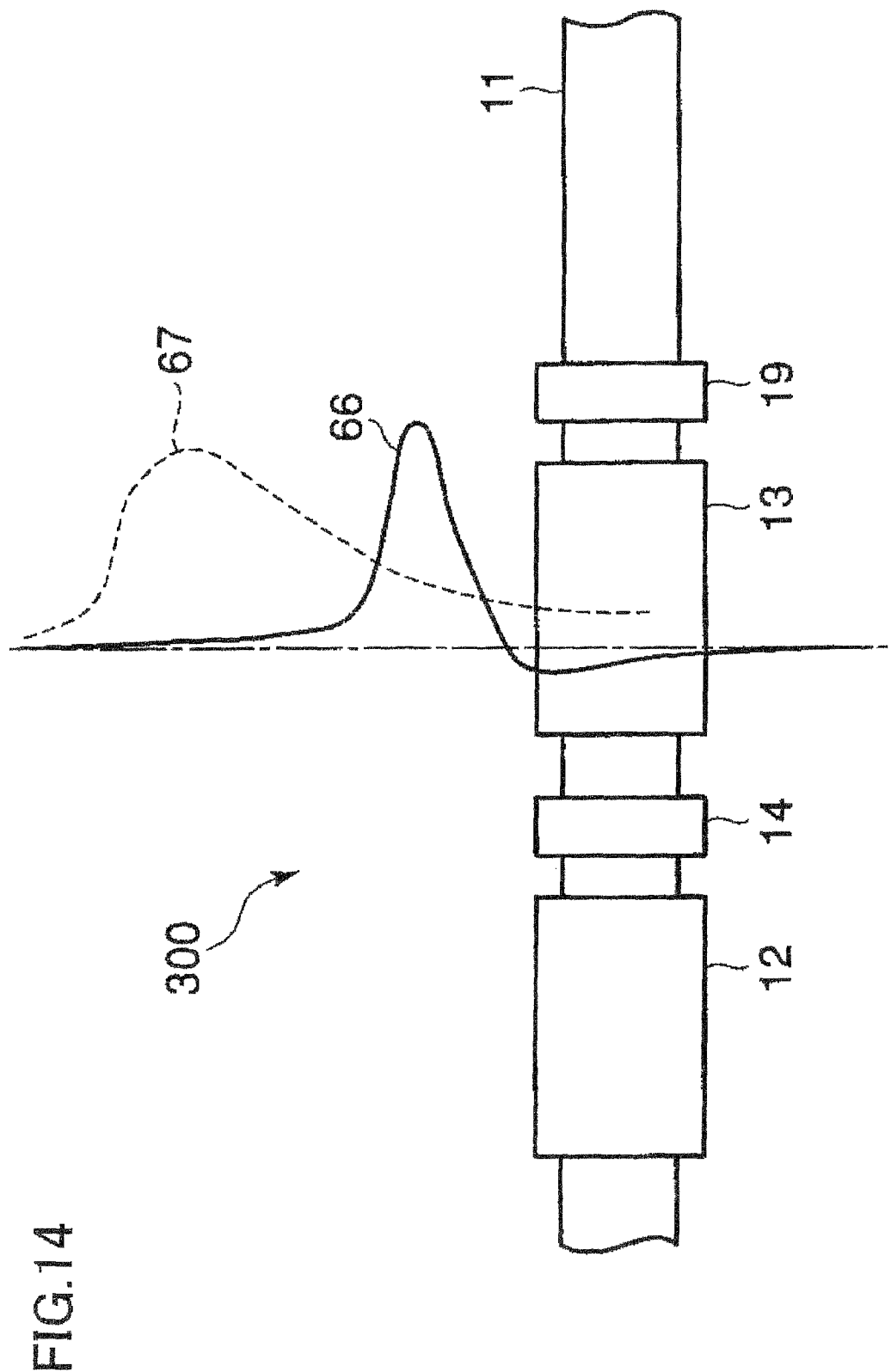
FIG. 14 shows spatial measurement characteristics of the sensor element 300 along the direction right angle to the radial direction.

FIG. 14 shows spatial measurement characteristics of the sensor element 300 along the direction right angle to z-axis (called as radial direction, hereinafter).

For the first connection state, the spatial measurement characteristics have high sensitivity at the place close to the sensor element 300 as denoted with 66. On the other hand, the spatial measurement characteristics have high sensitivity at the place which is far from the sensor element 300 for the second connection state as denoted with 67. Moreover, rather broad spatial measurement characteristics are obtained for the radial direction for the second connection state.

In the signal processing unit 73, the distance from the sensor element 300 to the substance that exists around the sensor element 300 can be precisely judged by analyzing two signals received by those two spatial measurement characteristics. By adding the spatially differentiating coil 19, the susceptibility in the plane (z-plane) perpendicular to z-axis can be high in the area of the blood vessel wall.

Instead of adding the selector switch 72, one more signal receiving circuit is added, by which the signals for the first connection state and the second connection state can simultaneously be received.

The external signal lead cabling from the sensor element 300, which comprises the signal receiving coil 13 that composes the second coil element and the spatially differentiating coils 14 and 19, is shown in FIG. 15A. Electrical wires are connected to the electrically connecting points Pa and Pb, which are those of the spatially differentiating coils 14 and 19, to the signal receiving coil 13, and the induced signals that are induced in these coils are externally led from the sensor element 300. The electrically leading wire is electrically connected to the selector switch 72.

Various modifications of the embodiments can be made from this embodiment. Some of them are explained as follows.

(1) The wound wire portion 13a, 14a and 19a that compose the signal receiving coil 13, and the spatially differentiating coils 14 and 19 can preferably be combined outside of the cylinder 11. As shown in FIG. 15B, the wound wire portion 13a, 14a and 19a may be independent wires which are led outside of the cylinder 11 in a form of three set of wires 13w, 14w and 19w so that the signal receiving coil 13, the spatially differentiating coil 14 and the spatially differentiating coil 19 are electrically connected in series.

Figure 16:
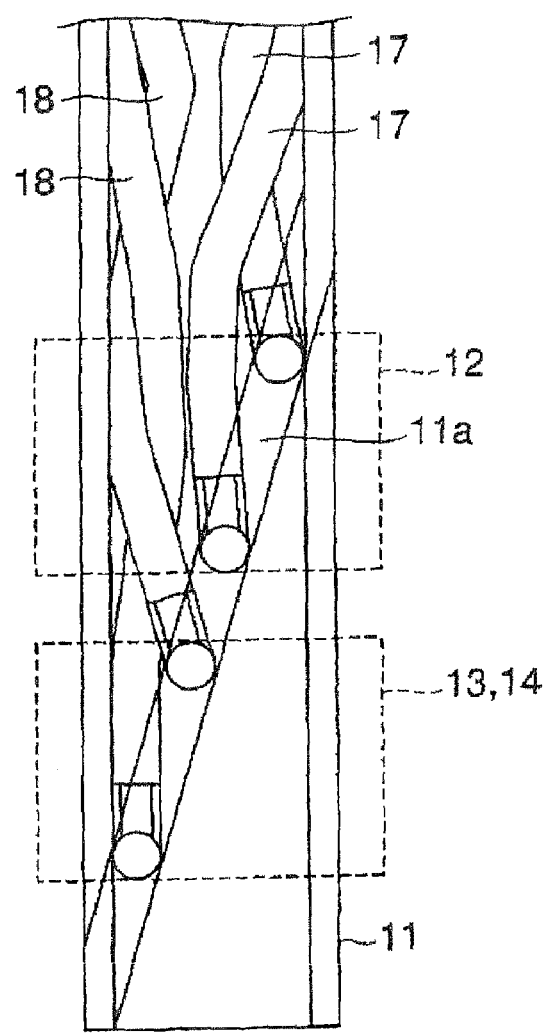

(2) The slit 11a formed in the sensor element 300 can preferably be in a slant angle against the central axis of the cylinder 11 as shown in FIG. 16. In FIG. 8, the slit 11a is parallel to the central axis of the cylinder 11. Since the positions where end portions of each coil are led into the inner space of the cylinder 11, the directions to the central axis from such positions are deviated for each of the coil, the electrical wires 17 and 18 can be easily the installed and laid out in the inner space of the cylinder 11 so that the assembly of the sensor element 300 can be facilitated.

Figure 17A:
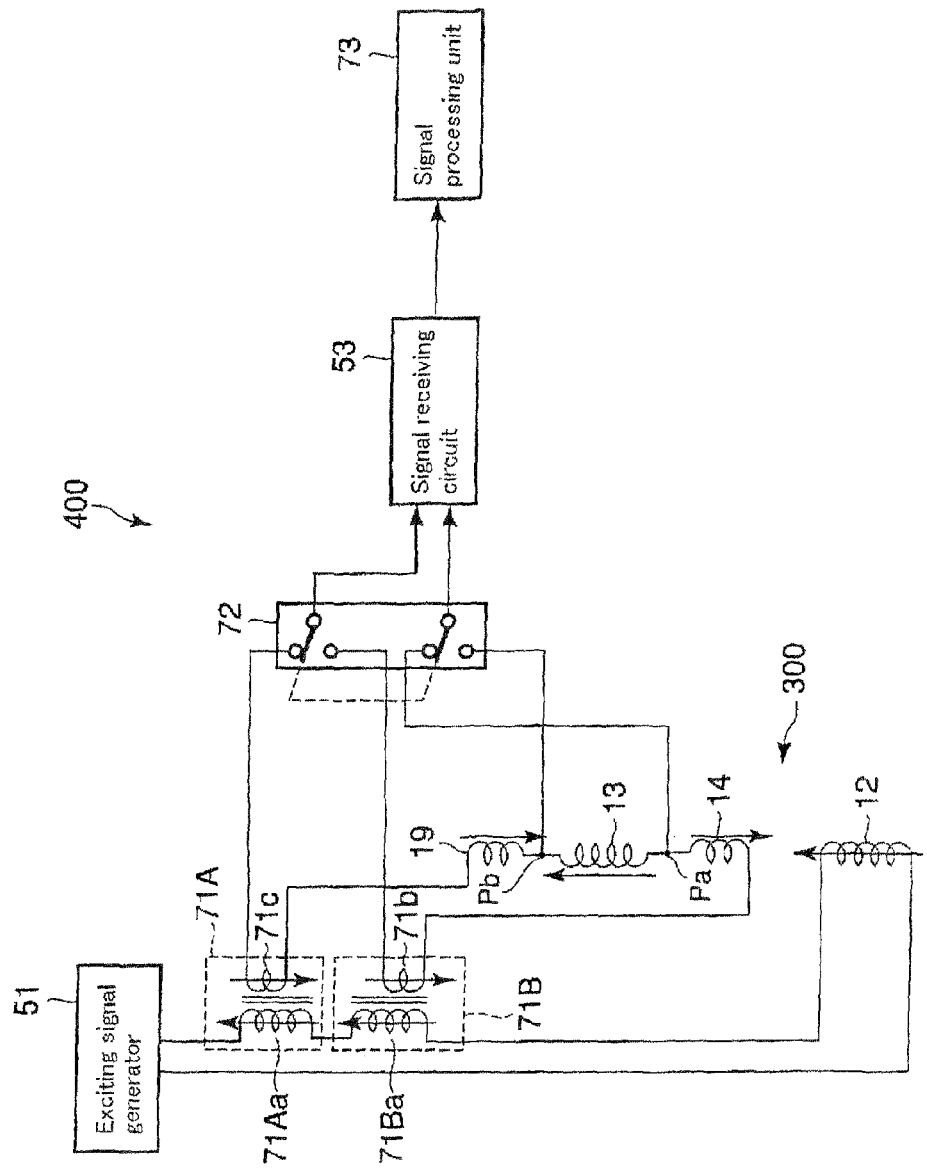
FIG. 17A is a circuit diagram of the composition of the sensor system 400 that has an external differential transformer composed of two independent external differential transformers.
Figure 17B:
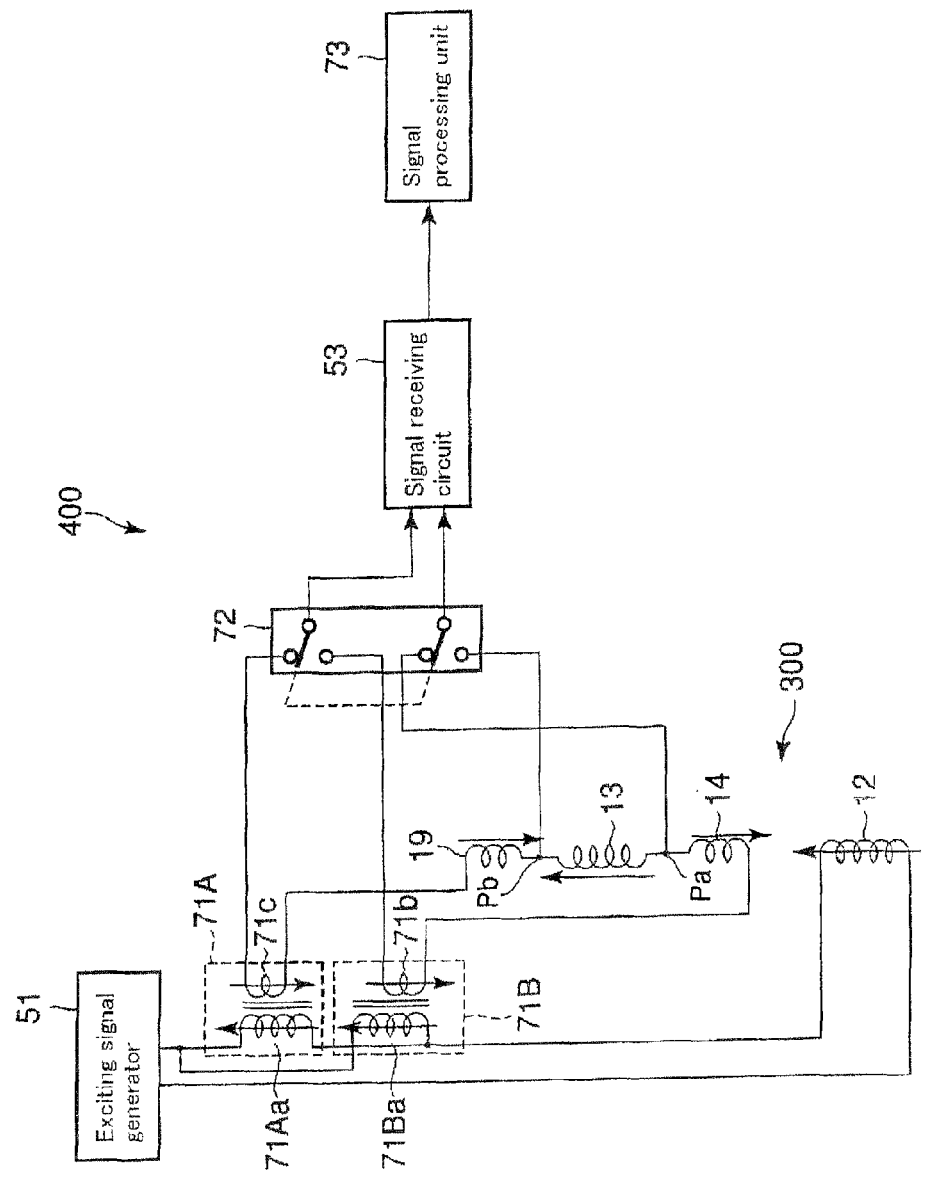
FIG. 17B is a circuit diagram of a composition of the sensor system 400 that has an external differential transformer composed of two independent external differential transformers.

(3) In the embodiment shown in FIG. 13, the external differential transformer 71 is composed of a single transformer. The external differential transformer 71 can be preferably composed of two independent transformers connected in series or in parallel. FIG. 17A shows the external differential transformer composed of two independent external differential transformers 71A and 71B connected in series. For this configuration, the primary coils are 71Aa and 71Ba to which secondary coils 71c and 71b are coupled, respectively. The electrical load of the exciting signal generator 51 is a summation of the impedances of the signal exciting coil 12 and two external differential transformer 71A and 71B. This modified embodiment uses two external differential transformers 71A and 71B, it is easy to adjust the induced signal induced by the signal receiving coil 13 and two spatially differentiating coils 14 and 19 to be zero by using the out of the external differential transformers 71A and 71B. On the other hand, FIG. 17B shows the external differential transformer composed of two independent external differential transformers 71A and 71B connected in parallel. For this configuration, the primary coils are 71Aa and 71Ba to which the secondary coils 71c and 71b are coupled, respectively. The electrical load of the exciting signal generator 51 is a summation of the impedance of the signal exciting coil 12 and the impedance that is an AC parallel summation of impedances of two external differential transformers 71A and 71B. In this modified embodiment, it is features that the zero point adjustment by using the external transformer 17B is less disturbed by the zero point adjustment by using the external differential transformer 17A when the exciting signal generator 51 has a low output impedance, in addition to being easy to adjust the induced signal induced by the signal receiving coil 13 and two spatially differentiating coils 14 and 19 to be zero by using the out of the external differential transformers 71A and 71B.

(4) The sensor elements 100 and 300 are preferred to be installed in catheters or balloon catheters.

Figure 18:
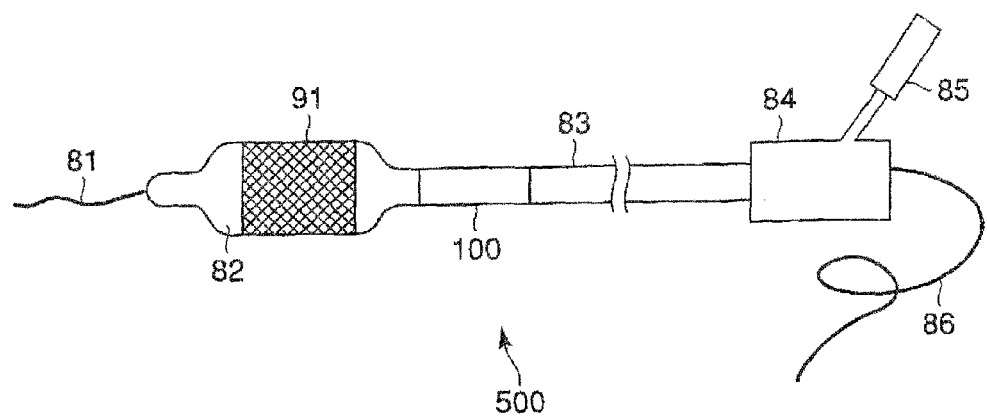
FIG. 18 is a drawing of an outer view of the balloon catheter 500 that equips with the sensor element 100.

FIG. 18 is a drawing that shows the outer view of a balloon catheter 500 that equips with the sensor element 100. The balloon catheter 500 as shown in FIG. 18 includes a guide wire 81, a balloon 82, a catheter sheath 83, a coupling manifold 84, a pump 85 and sensor element 100. A stent 91 is attached to the balloon 82 in FIG. 18.

The sensor element 100 is installed in the position close to the balloon 82 molded in the catheter sheath 83. However, the sensor element 100 is preferred to be installed ahead of balloon 82. The sensor element is connected to the exciting signal generator 51 by means of a cable 86 that is externally led out from the coupling manifold 84 through the inside or inner space of the catheter sheath 83, and is connected to the external differential transformer 52 and the signal receiving circuit 53.

The measurement method by using this balloon catheter 500 is explained as follows.

(4-1) Specifying Plaques

At the position where plaques exist in the blood vessels, the induced signal detected by the sensor element 100 decreases during movement of the sensor element which moves in the range of millimeters. This behavior of the induced signal is due to plaques forming in and along the blood vessel. More precisely, the plaques are gruelized or crystallized from adipo or lipo-cells that are mostly in the portion between the intima and the media, and, for incomplete plaques in the portion between the media and the adventitia, the electrical resistance is larger than that of blood. According to such behavior, the induced voltage obtained by the sensor element 100 is monitored while moving in the blood vessel after tapping the catheter sheath 83 to the blood vessel. The position where the induced voltage is smaller than that in neighboring position is specified as the position where plaques exist.

(4-2) Specifying Thrombi

At the position where thrombi exist, the thrombi protrude inside from the blood vessel wall, and the electrical resistance of the thrombi is larger than the blood. The length where the thrombi exist along the blood vessels is short. Therefore at the areas of the both sides of the protrusion of the thrombus along the blood vessel, relatively large induced signal is generated due to the characteristics of the electromagnetic induction field (which is called a formation bed effect in the technical field of oil exploration). Due to such effect, relatively large induced voltage is detected by the sensor element 100. The position where the thrombus exists is specified by the detection of such localized increase of induced voltage.

(4-3) Specifying Stent Diameter

By immersing the balloon catheter 500 in physiological saline or in artificial blood, the relation between the diameter of stent 91 and the induced voltage received by the signal receiving circuit 53 can be obtained to determine a correspondence between them. Also, the relation between the diameter of stent 91 and the induced voltage received by the signal receiving circuit 53 for the case when the balloon catheter 500 is left in the air can be obtained to determine a correspondence between them. For these correspondences, the induced voltage received by the signal receiving circuit 53 in the former case subtracted by that in the latter case creates a correction factor that represents the effects of the physiological saline or in artificial blood against the diameters of the stents. Before the operation, the above relation between the diameter of the specific stent to be used, a combination of such induced voltage and the correction factor are confirmed. In operation, the balloon 82, to which is equipped with a stent, is pushed up to and stays at the angio stenosis or infarction part in the blood vessel. Then the induced voltage Vm is measured in the area in the smooth blood vessel where no such angio stenosis or infarction part builds. The balloon 82 is inflated by sending air or physiological saline by the pump 85. The stent is expanded against the angio stenosis or infarction part and they stay there due to the tight contact to the intima of the blood vessel. Then the sensor element 100 of the balloon catheter 500 is moved to such area where the stent stays in the blood vessel and the induced voltage Vm−Va0 is measured which is a summation of voltage component (Vm) due to the blood and that (Va0) where the negative sign for Va0 is due to the differential measurement of the signal receiving circuit 53. From the induced voltage Vm−Va0, the induced voltage Vm which was obtained before is removed, and Va0 can then be obtained. According to the above relation that is given as the relation between the diameter of stent 91 and the induced voltage received by the signal receiving circuit 53 for the case when the balloon catheter 500 is left in the air, the diameter of the stent to which the voltage Va0 corresponds is judged as the specific diameter of the stent 91 staying in the blood vessel after expansion.

For the case when the sensor element 300 is used instead of the sensor element 100, two specific diameters for the stent 91 are obtained regarding the first connection state and the second connection state of the selector switch 72. The means of these two diameters are preferably determined as the diameter of the stent staying in the blood vessel after expansion.

(5) The signal exciting coil and the signal receiving coil may be exchanged in the sensor system so that the second coil element, which is an electrical coil, for which the signal receiving coil 13 and the spatially differentiating coil 14 are connected in series is used as an signal exciting coil, and the signal exciting coil 12 is used as a signal receiving coil. In this case, the same spatial detection to measure the diameters of the stents and diagnose the plaques and thrombi grown in the blood vessels is obtained due to the complementarity of signal exciting coil and signal receiving coil for the electromagnetic induction.

(6) For the electrical wires, twisted cables, shielded twisted pair cables or the wires composing thereof can be preferably used. The twisted cables have low decay of radio frequency. The twisted cable may comprise solid wires or twisted wires. The shielded twisted pair cables have low cross talks between the exciting signals and the receiving signal sand large S/N (signal-to-noise) ratio can be obtained for the receiving signals.

(7) The materials for the cylinder 11 can be preferably nylon (a trade mark), PEEK (a trade mark, Poly Ether Ether Ketone) or poly ether block amid.

(8) A cylinder 11 may preferably have a double layered structure, wherein the outer layer of the cylinder 11 is made of a highly slippery polymer and the inner layer of PEEK is not easily broken by the pressure from the outside. To keep its flexibility, a meshed PEEK may be preferably inserted in the cylinder 11.

(9) Polymers may be preferably filled in the inner space of the cylinder 11. With this filler, the cylinder 11 is not easily broken.

(10) It is possible to extend the lead portions of each coil to the outside of the cylinder 11 by which the electrical wires 17 and 18 can be removed and a simple structure of the sensor element 100 is obtained, since neither soldering nor soldering portion is necessary in the inner space of the cylinder 11. That leads to a small cross sectional area of the cylinder 11, and the outer diameter of the sensor element 100 can be made small so that catheters for the use of the capillary blood vessel can be realized.

(11) For the above embodiment, the determination of existence of the thrombi, plaques and stents in the blood vessels and the determination of the diameters of stents being set in the blood vessels based on the signals of induced voltages of the AC signal is carried out. In addition, the phase shift of the AC signal for the induced voltage against the exciting signal can be preferably used. This technology is that of phaser induction that is widely applied to the oil field equipments used for oil exploration (see Non-Patent Reference 1). For the use of phaser induction technology, the same number of the measurements done by detecting induced voltages of AC signals is obtained for the measurements done by the detecting phase shifts of AC signals in addition to detecting induced voltages. Therefore, it is possible to determine the diameters of the thrombi and plaques and specify their electrical resistivities. A PLL (Phase Locked Loop) circuitry may be preferably added to the signal processing systems 54 and 73 for the measurement of the phase shift.

(12) The determination of diameters and the electrical resistivities of the thrombi and plaques by means of AC differential signal and AC phase shift are based on two-variable model using AC differential signal and AC phase shift and two set of solutions for diameters and the electrical resistivities can be obtained. As a further practical determination of these parameters, there is a determination method, such as "table lookup", wherein the relation between the diameters and the electrical resistivities are obtained using such two-variable model beforehand. By the measurement of the actual AC differential signals and the phase shifts, the diameters and the electrical resistivities are determined by interpolation of measurement results listed in the table where the interpolation of the measurement is done by a process of "table lookup." These results can preferably be associated to the physiological and morphological parameters of the plaques, thrombosis obtained other diagnostic equipments.

(13) The signal generated for both terminals of the sensor element 300 is preferably received by the signal receiving circuit for the sensor system that uses the sensor element 300. The received signal for this sensor element 300 has less influence of the induction current Ib in comparison to the use of the sensor element 100 by reducing the induced current received by the signal receiving coil 13 by the induced current generated in the spatially differentiating coils 14 and 19 in a manner of an AC signal. This circuit configuration gives further improvement of sensitivity for AC signal detection that provides easier measurement.

The present invention is not limited within the embodiments as illustrated in the above drawings. The modification in the range of the same concept of the present invention and those which have combinations of plurality of the elements regarding these inventions in an appropriate method are included as a same or an equivalent invention thereto. The some of elements in the above embodiments can be omitted for the implementation without departing from the scope of the present invention.

What is claimed is:

1. A sensor element configured to be insertable into a human body, comprising:
   a cylinder having an outer surface, two ends, a longitudinal axis, an inner space with a diameter, an opening at at least one end of the cylinder, a slit of a predetermined width formed along the longitudinal axis of the cylinder, wherein the width of said slit is less than the diameter of an inner space of the cylinder;
   a coil element group having at least two coil elements, each of the coil elements is an electrical coil having a wound wire portion with two lead portions respectively formed at both ends of each of the coil elements, said wound wire portion is formed on the outer surface of said cylinder, and said two lead portions of each of the coil elements are led into said inner space of said cylinder by passing through said slit,
   and at least two pairs of electrically conductive wire set in said inner space, and each of the at least two pairs of electrically conductive wire is electrically connected to each of said two lead portions and is externally led out from said opening at one end of said cylinder.

2. A sensor element according to claim 1, wherein said slit is formed in a slant angle to a central axis of said inner space of the cylinder.

3. A sensor element according to claim 1, wherein said at least two pairs of electrically conductive wire is formed as an extension of each of said two lead portions.

4. A sensor element according to claim 1, wherein said pair of electrically conductive wire is a pair of electrical cables including conductive wires each connected to one of said two lead portions and an insulating sheath each covering said conductive wires.

5. A sensor element according to claim 1, wherein said pair of electrically conductive wire is a twisted pair cable, each of which pair cable is connected to one of said two lead portions.

6. A sensor element according to claim 1, wherein said pair of electrically conductive wire is a pair of patterned conducting layer formed on a flexible film and each of said patterned conducting layer has an electrical contact portion to which each of said lead portions is connected.

7. A sensor element according to claim 3, wherein said coil element group includes a first coil element and a second coil element,
   of which said first coil element has a wound wire portion including a wound wire with a first winding direction,
   of which said second coil element has a wound wire portion including a first wound wire with said first winding direction and a second wound wire with a second winding direction opposite of said first winding direction, wherein said first wound wire and said second wound wire of said second coil element are electrically connected through an electrically connecting portion.

8. A sensor element according to claim 3, wherein said coil element group comprises a first coil element and a second coil element,
   said second coil element includes a first wound wire portion with a first winding direction and a second wound wire portion, having a fewer number of wound turn than said first wound wire portion, and a third wound wire portion, wherein both said second wound wire portion and said third wound wire portion of said second coil element are wounded in a second direction opposite of said first winding direction, wherein said first wound wire portion locates between said second wound wire portion and said third wound wire portion of said second coil element, and said second wound wire portion locates between said first wound wire portion and said first coil element, one end of said first wound wire portion and one end of said second wound wire portion are electrically connected through a first electrically connecting portion, and said lead portions are formed at the other end of said second wound wire portion and the other end of said third wound wire portion.

9. A sensor element according to claim 7, wherein said first coil element has a first wound wire with said first winding direction and a second wound wire with the said second winding direction opposite to said first winding direction, and said first wound wire and said second wound wire are electrically connected through an electrically connecting portion.

10. A sensor element according to claim 7 further comprising a conductive leading wire electrically connected to said electrical portion and externally led out via said inner space of said cylinder.

11. A sensor system comprising said sensor element according to claim 7, further comprising an exciting signal generator and a signal receiving circuit,
wherein said first coil element is excited via said pair of electrically conductive wire by an exciting signal generated by said exciting signal generator, and
said second coil element having the first wound wire and the second wound wire is connected via another pair of electrically conductive wire to said signal receiving circuit that receives an induced signal in said second coil element.

12. A sensor system according to claim 11, further comprising a signal reducing module,
wherein one electrically conductive wire of said pair of electrically conductive wire, which locates between said first coil element and said exciting signal generator, is connected to said exciting signal generator via the signal reducing module,
one electrically conducting wire of said pair of electrically conductive wire, which locates between said second coil element and said signal receiving circuit, is connected to said signal receiving circuit that receives said induced signal via said signal reducing module,
and said induced signal is reduced by an exciting signal generated by said exciting signal generator.

13. A sensor system comprising said sensor element according to claim 8, further comprising an exciting signal generator, signal reducing module having a first signal reducing circuit and a second signal reducing circuit, a signal selector and a signal receiving circuit,
wherein said exciting signal generator generates an exciting signal, said first coil element receives the exciting signal from said exciting signal generator through said pair of electrically conductive wire,
said second coil element has two sets of electrically conductive leading wire,
wherein a first induced signal is induced in said second wound wire portion, said second wound wire portion of the second coil element is connected between said signal selector and said first signal reducing circuit,
wherein a second induced signal is induced in said third wound wire portion, said third wound wire portion of the second coil element is connected between said signal selector and the second signal reducing circuit,
and said signal receiving circuit is connected to said signal selector adapted to selectively provide either the first induced signal or the second induced signal to said receiving circuit.

14. A sensor system according to claim 12, wherein said signal reducing module is a coupling transformer having a primary coil and more than one of secondary coils, said exciting signal is directly, or via said first coil element, input to said primary coil, and said more than one of secondary coils is connected to said signal receiving circuit via at least said first wound wire portion of said second coil element.

15. A sensor system according a claim 12 further comprising an evaluation unit adapted to evaluate physical characteristics of a subject existing around said sensor element by using a signal received by said receiving circuit.

16. A sensor system according to claim 15, wherein said evaluation unit is further adapted to determine an existence of at least one subject selected from a plaque and a thrombus grown in and a stent installed in a blood vessel.

17. A sensor system according to claim 15, wherein said evaluation unit is further adapted to measure a diameter of said stent installed in said blood vessel.

18. A catheter comprising a catheter sheath in form of a tube, a sensor element according to claim 1, further comprising a cable electrically connected to an electrically conducting wire included in said sensor element and set in an inner space of said catheter sheath.

19. A catheter according to claim 18, further comprising a balloon inflatable by injecting fluid carried through said catheter sheath, wherein said sensor element is installed inside of said catheter sheath at a position close to said balloon.

20. A manufacturing method for a sensor element configured to be insertable into a human body, comprising:
using a plurality of electrical wires to form a plurality of coil elements comprising electrical coils, each of the electrical coils including at least one wound wire portion, and two lead portions formed in both ends of each of said plurality of coil elements, and
inserting each of said plurality of coil elements around a cylinder, the cylinder having a longitudinal axis, an inner space with a diameter, an opening at at least one end and a slit of a predetermined width formed along the longitudinal axis, wherein the width of said slit is less than the diameter of the inner space of the cylinder such that said coil elements surround said cylinder and both lead portions of said coil element are inserted into said inner space from said opening at said at least one end of said cylinder by sliding along said slit in a form that said lead portions extend into said inner space of said cylinder through said slit and a terminal of said electrical wires which are connected to said coil element so that a terminal of extension of each of said two lead portions extends to external of said inner space of said cylinder through said open end of said cylinder.

* * * * *